(12) United States Patent
Takahasi et al.

(10) Patent No.: US 11,127,116 B2
(45) Date of Patent: Sep. 21, 2021

(54) SURGERY CONTROL APPARATUS, SURGERY CONTROL METHOD, PROGRAM, AND SURGERY SYSTEM

(71) Applicant: SONY CORPORATION, Tokyo (JP)

(72) Inventors: Kenji Takahasi, Kanagawa (JP); Kentaro Fukazawa, Tokyo (JP); Hisakazu Shiraki, Kanagawa (JP); Masahito Yamane, Kanagawa (JP); Takeshi Uemori, Tokyo (JP)

(73) Assignee: SONY CORPORATION, Tokyo (JP)

( * ) Notice: Subject to any disclaimer, the term of this patent is extended or adjusted under 35 U.S.C. 154(b) by 13 days.

(21) Appl. No.: 15/761,344

(22) PCT Filed: Nov. 21, 2016

(86) PCT No.: PCT/JP2016/084380
§ 371 (c)(1),
(2) Date: Mar. 19, 2018

(87) PCT Pub. No.: WO2017/094535
PCT Pub. Date: Jun. 8, 2017

(65) Prior Publication Data
US 2018/0268523 A1 Sep. 20, 2018

(30) Foreign Application Priority Data
Dec. 1, 2015 (JP) .............................. JP2015-234744

(51) Int. Cl.
*G06T 3/40* (2006.01)
*A61B 1/00* (2006.01)
(Continued)

(52) U.S. Cl.
CPC .......... *G06T 3/4069* (2013.01); *A61B 1/0002* (2013.01); *A61B 1/0005* (2013.01);
(Continued)

(58) Field of Classification Search
CPC ................. G06T 3/4069; G06T 7/0014; G06T 2207/10024; G06T 2207/10068;
(Continued)

(56) References Cited

U.S. PATENT DOCUMENTS 4,213,145 A * 7/1980 Nagumo ........... H01L 27/14868
257/E27.159
4,357,624 A * 11/1982 Greenberg ............ G06T 11/001
348/578
(Continued)

FOREIGN PATENT DOCUMENTS

| JP | 2003-32538 A | 1/2003 |
|---|---|---|
| JP | 2005-115789 A | 4/2005 |

(Continued)

OTHER PUBLICATIONS

Young, Alias-free image subsampling using fourier-based windowing methods, 2004 (Year: 2004).*

(Continued)

*Primary Examiner* — Charles L Beard
(74) *Attorney, Agent, or Firm* — Xsensus, LLP

(57) ABSTRACT

A medical system including a medical imaging device, and circuitry that obtains a plurality of first images each having a different phase from the medical imaging device, combines each of the plurality of first images a plurality of times to generate a plurality of second images, wherein each time of the plurality of times that the plurality of first images are combined, a different candidate process is used in the combining, and selects one image from the plurality of second images as an output image for display, the selected one image being higher quality than any one of the plurality of first images.

20 Claims, 13 Drawing Sheets

(51) Int. Cl.
  *A61B 1/015* (2006.01)
  *A61B 1/04* (2006.01)
  *A61B 1/06* (2006.01)
  *A61B 1/313* (2006.01)
  *G06T 7/00* (2017.01)

(52) U.S. Cl.
  CPC ...... *A61B 1/00006* (2013.01); *A61B 1/00039* (2013.01); *A61B 1/015* (2013.01); *A61B 1/04* (2013.01); *A61B 1/0669* (2013.01); *A61B 1/3132* (2013.01); *G06T 7/0014* (2013.01); *G06T 2207/10024* (2013.01); *G06T 2207/10068* (2013.01); *G06T 2207/20212* (2013.01)

(58) Field of Classification Search
  CPC ...... G06T 2207/20212; A61B 1/00006; A61B 1/0002; A61B 1/00039; A61B 1/0005; A61B 1/015; A61B 1/04; A61B 1/0669; A61B 1/3132
  See application file for complete search history.

(56) References Cited

U.S. PATENT DOCUMENTS

| | | | | |
|---|---|---|---|---|
| 5,168,350 A * | | 12/1992 | Shinozaki | H04N 5/332 348/262 |
| 5,184,212 A * | | 2/1993 | Yamamoto | H04N 9/045 348/234 |
| 5,255,081 A * | | 10/1993 | Miyamoto | H04N 9/045 348/234 |
| 5,272,524 A * | | 12/1993 | Nagumo | H04N 9/045 341/61 |
| 5,343,311 A * | | 8/1994 | Morag | G06T 11/001 358/500 |
| 5,398,066 A * | | 3/1995 | Martinez-Uriegas | H04N 11/044 375/240.25 |
| 5,418,564 A * | | 5/1995 | Aoki | H04N 1/486 348/262 |
| 5,528,292 A * | | 6/1996 | Ikeda | G06T 3/4007 348/222.1 |
| 5,541,653 A * | | 7/1996 | Peters | H04N 9/8047 348/264 |
| 5,726,709 A * | | 3/1998 | Kinoshita | H04N 9/045 348/264 |
| 5,867,285 A * | | 2/1999 | Hirota | G06T 5/20 358/520 |
| 5,982,850 A * | | 11/1999 | Nagata | H04N 9/646 348/265 |
| 6,002,518 A * | | 12/1999 | Faris | G02B 27/0093 359/465 |
| 6,048,316 A * | | 4/2000 | Zhao | G01S 7/52034 600/447 |
| 6,101,238 A * | | 8/2000 | Murthy | G01N 23/04 378/62 |
| 6,126,599 A * | | 10/2000 | Jago | G01S 7/52025 600/437 |
| 6,205,259 B1 * | | 3/2001 | Komiya | G06T 5/50 382/284 |
| 6,278,492 B1 * | | 8/2001 | Nakamura | H04N 5/232 348/441 |
| 6,442,289 B1 * | | 8/2002 | Olsson | G01S 7/52034 382/128 |
| 6,466,618 B1 * | | 10/2002 | Messing | G06T 3/4069 348/42 |
| 6,593,558 B1 * | | 7/2003 | Edgar | G01J 3/50 250/208.1 |
| 6,650,772 B1 * | | 11/2003 | Inoue | G06T 11/001 358/518 |
| 6,747,648 B2 * | | 6/2004 | Hoehn | G06T 11/60 345/428 |
| 6,795,585 B1 * | | 9/2004 | Parada | G06T 5/00 358/523 |
| 6,956,973 B1 * | | 10/2005 | Liang | H04N 19/647 375/E7.047 |
| 7,120,297 B2 * | | 10/2006 | Simard | G06K 9/00456 382/166 |
| 7,602,997 B2 * | | 10/2009 | Young | G06T 3/4069 382/280 |
| 7,689,909 B1 * | | 3/2010 | Szuszczewicz | H04N 1/00132 715/204 |
| 7,837,624 B1 * | | 11/2010 | Hossack | G01S 7/52065 600/443 |
| 7,856,154 B2 * | | 12/2010 | Young | G06T 3/4069 382/299 |
| 8,436,909 B2 * | | 5/2013 | Farina | H04N 9/045 348/218.1 |
| 8,538,074 B2 * | | 9/2013 | Nakamura | G06T 11/60 382/103 |
| 8,553,093 B2 * | | 10/2013 | Wong | H04N 5/23232 348/208.13 |
| 8,577,184 B2 * | | 11/2013 | Young | G06T 3/4069 382/299 |
| 8,619,082 B1 * | | 12/2013 | Ciurea | G06T 7/557 345/427 |
| 8,666,196 B2 * | | 3/2014 | Young | G06T 3/4069 382/299 |
| 8,704,901 B2 * | | 4/2014 | Numata | H04N 5/3572 348/208.6 |
| 8,831,367 B2 * | | 9/2014 | Venkataraman | H04N 19/70 382/233 |
| 8,861,822 B2 * | | 10/2014 | Pagoulatos | A61B 8/13 382/131 |
| 8,983,164 B2 * | | 3/2015 | Iwase | A61B 3/1225 382/131 |
| 9,013,611 B1 * | | 4/2015 | Szedo | G06T 3/4015 348/242 |
| 9,135,292 B1 * | | 9/2015 | Tsun | G06F 16/958 |
| 9,185,276 B2 * | | 11/2015 | Rodda | H01L 27/14621 |
| 9,218,323 B2 * | | 12/2015 | Damera-Venkata | G06F 40/106 |
| 9,247,136 B2 * | | 1/2016 | Emmett | H04N 5/23245 |
| 9,338,414 B2 * | | 5/2016 | Kamiya | G06T 3/4015 |
| 9,420,175 B2 * | | 8/2016 | Furukawa | G06T 5/002 |
| 9,536,045 B1 * | | 1/2017 | Fram | G16H 30/20 |
| 9,736,447 B2 * | | 8/2017 | Hirota | G06T 7/90 |
| 9,813,616 B2 * | | 11/2017 | Lelescu | G06T 3/4069 |
| 9,875,552 B1 * | | 1/2018 | Savage | G06T 7/246 |
| 9,892,695 B2 * | | 2/2018 | Nishiike | G09G 3/344 |
| 9,928,575 B2 * | | 3/2018 | Takatori | G06K 9/4604 |
| 10,074,589 B1 * | | 9/2018 | Jesensky | G06Q 30/0269 |
| 10,074,682 B2 * | | 9/2018 | Toda | H01L 27/14605 |
| 10,119,808 B2 * | | 11/2018 | Venkataraman | G06T 7/40 |
| 10,182,216 B2 * | | 1/2019 | Mullis | H04N 9/093 |
| 10,250,871 B2 * | | 4/2019 | Ciurea | G06T 7/80 |
| 10,264,236 B2 * | | 4/2019 | Kiniwa | A61B 90/20 |
| 10,373,292 B2 * | | 8/2019 | Hsiao | G06T 7/13 |
| 10,423,713 B1 * | | 9/2019 | Cooper | G06F 3/0484 |
| 10,452,920 B2 * | | 10/2019 | Kauffmann | H04N 5/144 |
| 10,469,814 B2 * | | 11/2019 | Kaji | G06T 7/60 |
| 10,636,126 B2 * | | 4/2020 | Kajimura | H04N 5/23232 |
| 10,650,505 B2 * | | 5/2020 | Kumar | G06T 5/50 |
| 2002/0113885 A1 * | | 8/2002 | Inoue | H04N 5/217 348/280 |
| 2002/0122067 A1 * | | 9/2002 | Geigel | G06T 11/60 715/788 |
| 2002/0165799 A1 * | | 11/2002 | Jaffe | G06Q 30/02 705/27.1 |
| 2002/0172287 A1 * | | 11/2002 | Kim | H04N 19/53 375/240.16 |
| 2002/0176120 A1 * | | 11/2002 | O'Callaghan | H04N 1/38 358/453 |
| 2003/0095723 A1 * | | 5/2003 | Ishizaka | G06T 3/4007 382/298 |
| 2004/0013319 A1 * | | 1/2004 | Wenstrand | H04N 5/349 382/299 |
| 2004/0080639 A1 * | | 4/2004 | Ishiga | H04N 9/045 348/272 |

(56) References Cited

U.S. PATENT DOCUMENTS

| | | | |
|---|---|---|---|
| 2004/0085330 A1* | 5/2004 | Walker, Jr. | G06Q 30/0276 345/630 |
| 2004/0156548 A1* | 8/2004 | Kodama | H04N 19/46 382/232 |
| 2004/0239885 A1* | 12/2004 | Jaynes | H04N 9/3147 353/30 |
| 2005/0007468 A1* | 1/2005 | Stavely | H04N 5/23293 348/239 |
| 2005/0111759 A1* | 5/2005 | Perlmutter | G06K 9/00758 382/294 |
| 2005/0134699 A1* | 6/2005 | Nagashima | G02B 13/0055 348/218.1 |
| 2005/0163402 A1* | 7/2005 | Aiso | G06T 3/4069 382/300 |
| 2005/0190972 A1* | 9/2005 | Thomas | G06K 9/209 382/218 |
| 2005/0268227 A1* | 12/2005 | Carlson | G06F 40/186 715/223 |
| 2006/0023089 A1* | 2/2006 | Kobayashi | H04N 19/59 348/234 |
| 2006/0058624 A1* | 3/2006 | Kimura | A61B 5/7445 600/407 |
| 2006/0067574 A1* | 3/2006 | Perlmutter | G06T 5/50 382/164 |
| 2006/0109358 A1* | 5/2006 | Song | H04N 9/045 348/275 |
| 2006/0114479 A1* | 6/2006 | John | G06T 3/4053 358/1.2 |
| 2006/0159369 A1* | 7/2006 | Young | G06T 3/4069 382/299 |
| 2006/0244842 A1* | 11/2006 | Hatano | H04N 9/045 348/223.1 |
| 2006/0257048 A1* | 11/2006 | Lin | G06K 9/00711 382/276 |
| 2006/0279555 A1* | 12/2006 | Ono | G06T 11/60 345/173 |
| 2006/0279585 A1* | 12/2006 | Milanfar | G06T 5/003 345/694 |
| 2006/0285007 A1* | 12/2006 | Yuyama | H04N 5/23248 348/362 |
| 2007/0024879 A1* | 2/2007 | Hamilton, Jr. | H04N 9/045 358/1.9 |
| 2007/0047834 A1* | 3/2007 | Connell | G06T 5/002 382/274 |
| 2007/0098299 A1* | 5/2007 | Matsumoto | G06T 15/08 382/284 |
| 2007/0159535 A1* | 7/2007 | Kumagai | H04N 5/2254 348/218.1 |
| 2007/0160310 A1* | 7/2007 | Tanida | H04N 5/2254 382/276 |
| 2007/0167801 A1* | 7/2007 | Webler | A61B 8/445 600/459 |
| 2007/0172126 A1* | 7/2007 | Kitamura | G06K 9/00228 382/190 |
| 2007/0175998 A1* | 8/2007 | Lev | H04N 1/00374 235/454 |
| 2007/0183682 A1* | 8/2007 | Weiss | G06T 5/20 382/261 |
| 2007/0204209 A1* | 8/2007 | Truelove | G06F 16/4393 715/203 |
| 2007/0211928 A1* | 9/2007 | Weng | G06T 7/0012 382/128 |
| 2007/0222878 A1* | 9/2007 | Tanifuji | H04N 3/155 348/294 |
| 2008/0037906 A1* | 2/2008 | Yano | H04N 9/045 382/312 |
| 2008/0069458 A1* | 3/2008 | Vega-Higuera | G06T 15/08 382/232 |
| 2008/0165843 A1* | 7/2008 | Dvir | H04N 19/61 375/240.01 |
| 2008/0219503 A1* | 9/2008 | Di Venuto | G06K 9/6857 382/103 |
| 2008/0247638 A1* | 10/2008 | Tanida | G06T 7/557 382/154 |
| 2008/0258725 A1* | 10/2008 | Hetherington | G01R 33/243 324/307 |
| 2008/0260292 A1* | 10/2008 | Tanaka | H04N 9/3188 382/299 |
| 2008/0291319 A1* | 11/2008 | Jannard | G06T 3/4015 348/345 |
| 2008/0298639 A1* | 12/2008 | Tsunekawa | G06T 3/4007 382/107 |
| 2008/0316323 A1* | 12/2008 | Morita | G06K 9/0004 348/222.1 |
| 2009/0060281 A1* | 3/2009 | Tanida | G06T 3/00 382/106 |
| 2009/0109480 A1* | 4/2009 | Osaka | G06F 40/103 358/1.15 |
| 2009/0110070 A1* | 4/2009 | Takahashi | H04N 19/60 375/240.12 |
| 2009/0112095 A1* | 4/2009 | Daigle | A61B 8/06 600/454 |
| 2009/0127430 A1* | 5/2009 | Hirasawa | G03B 15/00 250/201.8 |
| 2009/0136102 A1* | 5/2009 | Kimpe | G06T 7/32 382/128 |
| 2009/0153694 A1* | 6/2009 | Takayama | G06T 3/4053 348/222.1 |
| 2009/0167893 A1* | 7/2009 | Susanu | G06T 5/009 348/224.1 |
| 2009/0168128 A1* | 7/2009 | Matsuzaki | G06K 9/209 358/518 |
| 2009/0182224 A1* | 7/2009 | Shmarak | A61B 5/7275 600/424 |
| 2009/0208080 A1* | 8/2009 | Grau | G06T 5/50 382/131 |
| 2009/0208115 A1* | 8/2009 | Abe | G06T 7/337 382/209 |
| 2009/0268984 A1* | 10/2009 | Intwala | G06T 7/32 382/294 |
| 2009/0326383 A1* | 12/2009 | Barnes | A61B 5/0059 600/476 |
| 2010/0008588 A1* | 1/2010 | Feldkhun | G01B 11/2518 382/206 |
| 2010/0013963 A1* | 1/2010 | Jannard | H04N 5/3675 348/242 |
| 2010/0023863 A1* | 1/2010 | Cohen-Martin | G06Q 30/02 715/723 |
| 2010/0036719 A1* | 2/2010 | Eklund | G06Q 30/0241 705/14.4 |
| 2010/0046842 A1* | 2/2010 | Conwell | G06K 9/32 382/218 |
| 2010/0067822 A1* | 3/2010 | Young | G06T 3/4069 382/264 |
| 2010/0097491 A1* | 4/2010 | Farina | H04N 5/232 348/223.1 |
| 2010/0097495 A1* | 4/2010 | Choe | H04N 5/23232 348/235 |
| 2010/0128928 A1* | 5/2010 | Ishiwatari | G06T 3/4053 382/103 |
| 2010/0131890 A1* | 5/2010 | Natanzon | G06F 3/0481 715/808 |
| 2010/0150437 A1* | 6/2010 | Morales | H04N 1/00196 382/167 |
| 2010/0157352 A1* | 6/2010 | Morales | G06F 3/04845 358/1.15 |
| 2010/0165088 A1* | 7/2010 | Seo | A61B 1/273 348/65 |
| 2010/0168881 A1* | 7/2010 | Weber | G11B 27/034 700/94 |
| 2010/0169389 A1* | 7/2010 | Weber | G11B 27/038 707/804 |
| 2010/0169777 A1* | 7/2010 | Weber | G11B 27/3027 715/716 |
| 2010/0169783 A1* | 7/2010 | Weber | G06F 40/106 715/731 |
| 2010/0169784 A1* | 7/2010 | Weber | G11B 27/034 715/731 |

(56) References Cited

U.S. PATENT DOCUMENTS

| | | | |
|---|---|---|---|
| 2010/0180234 A1* | 7/2010 | Szuszczewicz | H04N 1/00196 715/838 |
| 2010/0182482 A1* | 7/2010 | Tanaka | G09G 3/3611 348/333.12 |
| 2010/0199227 A1* | 8/2010 | Xiao | G06F 3/0481 715/863 |
| 2010/0271515 A1* | 10/2010 | Imagawa | H04N 5/144 348/266 |
| 2010/0280781 A1* | 11/2010 | Winter | G02B 23/26 702/104 |
| 2010/0283847 A1* | 11/2010 | Aikawa | G01N 21/8803 348/142 |
| 2010/0284628 A1* | 11/2010 | Uebayashi | A61B 6/032 382/275 |
| 2010/0302418 A1* | 12/2010 | Adams, Jr. | H04N 9/07 348/281 |
| 2010/0318467 A1* | 12/2010 | Porter | H04N 5/2624 705/51 |
| 2010/0329550 A1* | 12/2010 | Cheatle | G06T 3/00 382/165 |
| 2011/0025905 A1* | 2/2011 | Tanaka | H04N 9/045 348/362 |
| 2011/0037845 A1* | 2/2011 | Mensink | G06T 3/4069 348/78 |
| 2011/0047513 A1* | 2/2011 | Onogi | H04N 5/44543 715/838 |
| 2011/0050935 A1* | 3/2011 | Mukherjee | H04N 19/597 348/222.1 |
| 2011/0080487 A1* | 4/2011 | Venkataraman | H04N 5/2253 348/218.1 |
| 2011/0105898 A1* | 5/2011 | Guthart | A61B 1/04 600/437 |
| 2011/0115934 A1* | 5/2011 | Wang | H04N 5/23248 348/222.1 |
| 2011/0128295 A1* | 6/2011 | Kimoto | G06F 16/58 345/589 |
| 2011/0142366 A1* | 6/2011 | Young | G06T 3/4069 382/274 |
| 2011/0150331 A1* | 6/2011 | Young | G06T 3/4069 382/167 |
| 2011/0154240 A1* | 6/2011 | Yamamoto | G06F 40/103 715/771 |
| 2011/0157609 A1* | 6/2011 | Brady | G06T 11/60 358/1.6 |
| 2011/0160543 A1* | 6/2011 | Parsey | A61B 6/501 600/300 |
| 2011/0170801 A1* | 7/2011 | Lu | G06T 3/4007 382/298 |
| 2011/0200270 A1* | 8/2011 | Kameyama | G06T 1/00 382/260 |
| 2011/0211732 A1* | 9/2011 | Rapaport | H04N 5/232 382/107 |
| 2011/0221764 A1* | 9/2011 | Callens | G06F 9/451 345/625 |
| 2011/0279652 A1* | 11/2011 | Eggert | G06T 7/593 348/47 |
| 2011/0292258 A1* | 12/2011 | Adler | G02B 23/2423 348/263 |
| 2012/0019696 A1* | 1/2012 | Tai | H01L 27/14621 348/280 |
| 2012/0020648 A1* | 1/2012 | Yamaji | G11B 27/034 386/278 |
| 2012/0035963 A1* | 2/2012 | Qian | G16H 15/00 705/3 |
| 2012/0081386 A1* | 4/2012 | Wiemker | G06T 19/00 345/589 |
| 2012/0089008 A1* | 4/2012 | Strehl | G01R 33/286 600/411 |
| 2012/0105681 A1* | 5/2012 | Morales | H04N 5/235 348/239 |
| 2012/0105691 A1* | 5/2012 | Waqas | G06T 3/4069 348/280 |
| 2012/0131498 A1* | 5/2012 | Gross | G06F 16/54 715/788 |
| 2012/0147205 A1* | 6/2012 | Lelescu | H04N 13/128 348/218.1 |
| 2012/0154608 A1* | 6/2012 | Ko | G11B 27/34 348/207.11 |
| 2012/0176408 A1* | 7/2012 | Moriya | A61B 5/0013 345/629 |
| 2012/0183193 A1* | 7/2012 | Weis | G06K 9/4614 382/131 |
| 2012/0189195 A1* | 7/2012 | Paik | H04N 9/045 382/164 |
| 2012/0198384 A1* | 8/2012 | Kumamoto | G06F 3/04855 715/786 |
| 2012/0206582 A1* | 8/2012 | DiCarlo | G06T 3/4015 348/71 |
| 2012/0207452 A1* | 8/2012 | Wang | G11B 27/034 386/280 |
| 2012/0210232 A1* | 8/2012 | Wang | G11B 27/34 715/723 |
| 2012/0213452 A1* | 8/2012 | Matsuyama | G06T 3/4053 382/294 |
| 2012/0223217 A1* | 9/2012 | Zheng | B01L 3/508 250/215 |
| 2012/0224766 A1* | 9/2012 | Ohki | H04N 5/23232 382/162 |
| 2012/0239506 A1* | 9/2012 | Saunders | G06Q 30/02 705/14.67 |
| 2012/0262607 A1* | 10/2012 | Shimura | H04N 5/2258 348/239 |
| 2012/0269444 A1* | 10/2012 | Naito | H04N 5/23254 382/197 |
| 2012/0274798 A1* | 11/2012 | Takahashi | H04N 9/735 348/222.1 |
| 2012/0281126 A1* | 11/2012 | Fossum | H04N 5/2355 348/302 |
| 2012/0294514 A1* | 11/2012 | Saunders | G06K 9/00677 382/159 |
| 2013/0088512 A1* | 4/2013 | Suzuki | G16H 10/60 345/629 |
| 2013/0093781 A1* | 4/2013 | Suzuki | A61B 6/461 345/581 |
| 2013/0094713 A1* | 4/2013 | Nanri | G01C 11/06 382/106 |
| 2013/0100333 A1* | 4/2013 | Awatsuji | G03H 1/0443 348/335 |
| 2013/0128068 A1* | 5/2013 | Georgiev | H04N 9/045 348/222.1 |
| 2013/0145241 A1* | 6/2013 | Salama | G06F 40/103 715/202 |
| 2013/0195429 A1* | 8/2013 | Fay | G11B 27/034 386/278 |
| 2013/0322530 A1* | 12/2013 | Rossato | H04N 19/63 375/240.12 |
| 2013/0326333 A1* | 12/2013 | Hashmi | G06F 16/957 715/234 |
| 2013/0335596 A1* | 12/2013 | Demandolx | H04N 5/772 348/231.99 |
| 2013/0335598 A1* | 12/2013 | Gustavsson | H04N 5/2351 348/234 |
| 2014/0009579 A1* | 1/2014 | Sumi | H04N 13/327 348/46 |
| 2014/0055797 A1* | 2/2014 | Obayashi | G06K 15/1878 358/1.9 |
| 2014/0055818 A1* | 2/2014 | Akaishi | H04N 1/4078 358/2.1 |
| 2014/0078346 A1* | 3/2014 | Imade | G06T 3/4053 348/234 |
| 2014/0085502 A1* | 3/2014 | Lin | H04N 5/2258 348/223.1 |
| 2014/0118529 A1* | 5/2014 | Zheng | G21K 7/00 348/80 |
| 2014/0133702 A1* | 5/2014 | Zheng | G06K 9/00624 382/103 |
| 2014/0136962 A1* | 5/2014 | Fischer | H04N 1/3872 715/250 |

(56) References Cited

U.S. PATENT DOCUMENTS

| | | | | |
|---|---|---|---|---|
| 2014/0139642 A1* | 5/2014 | Ni | G06T 7/90 | 348/48 |
| 2014/0147013 A1* | 5/2014 | Shandas | A61B 8/5246 | 382/107 |
| 2014/0226036 A1* | 8/2014 | Jannard | H04N 9/64 | 348/231.99 |
| 2014/0226150 A1* | 8/2014 | Colonna de Lega | G01B 11/2441 | 356/73 |
| 2014/0245115 A1* | 8/2014 | Zhang | G06F 3/04842 | 715/202 |
| 2014/0267351 A1* | 9/2014 | Klaus | H04N 5/332 | 345/589 |
| 2014/0307140 A1* | 10/2014 | Hayashi | H04N 9/07 | 348/281 |
| 2014/0307971 A1 | 10/2014 | Hanzawa | | |
| 2014/0328462 A1* | 11/2014 | Uehara | A61B 6/5235 | 378/62 |
| 2014/0331124 A1* | 11/2014 | Downs | G06F 40/106 | 715/243 |
| 2014/0379382 A1* | 12/2014 | Morishima | G06F 19/321 | 705/3 |
| 2014/0380171 A1* | 12/2014 | Maloney | H04N 1/00183 | 715/732 |
| 2015/0003708 A1* | 1/2015 | Prevrhal | G06T 5/50 | 382/131 |
| 2015/0005659 A1* | 1/2015 | Masumoto | A61B 6/032 | 600/538 |
| 2015/0025718 A1* | 1/2015 | Miichi | G06F 3/0486 | 701/21 |
| 2015/0046791 A1* | 2/2015 | Isaacson | G06F 40/146 | 715/234 |
| 2015/0124114 A1* | 5/2015 | Kamiya | G06T 3/4015 | 348/222.1 |
| 2015/0138346 A1* | 5/2015 | Venkataraman | G06T 7/596 | 348/135 |
| 2015/0144693 A1* | 5/2015 | Li | G06K 7/1473 | 235/437 |
| 2015/0154356 A1* | 6/2015 | Alvarez Del Castillo | G06F 19/321 | 715/853 |
| 2015/0169207 A1* | 6/2015 | Mody | G06F 9/451 | 715/763 |
| 2015/0178786 A1* | 6/2015 | Claessens | G06Q 30/0269 | 705/14.66 |
| 2015/0187048 A1* | 7/2015 | Yang | G06T 3/4069 | 345/660 |
| 2015/0206169 A1* | 7/2015 | Ye | G06Q 30/0242 | 705/14.41 |
| 2015/0206280 A1* | 7/2015 | Ono | G06T 3/4069 | 348/223.1 |
| 2015/0206300 A1* | 7/2015 | Nowinski | G06T 7/0014 | 382/131 |
| 2015/0229898 A1* | 8/2015 | Rivard | H04N 5/2353 | 348/223.1 |
| 2015/0229932 A1* | 8/2015 | Sato | H04N 19/159 | 375/240.12 |
| 2015/0242374 A1* | 8/2015 | Kong | G06F 40/106 | 715/201 |
| 2015/0260509 A1* | 9/2015 | Kofman | G01B 11/2504 | 356/601 |
| 2015/0279033 A1* | 10/2015 | Murakami | G06T 7/136 | 382/128 |
| 2015/0281570 A1* | 10/2015 | Takamura | G06K 9/6215 | 348/241 |
| 2015/0288941 A1* | 10/2015 | Schachter | G06T 5/50 | 348/164 |
| 2015/0302612 A1* | 10/2015 | Ishikawa | G06T 11/40 | 345/590 |
| 2015/0310613 A1* | 10/2015 | Murakami | H04N 5/23229 | 382/128 |
| 2015/0317434 A1* | 11/2015 | Kondo | A61B 5/00 | 705/3 |
| 2015/0319363 A1* | 11/2015 | Furukawa | G06T 11/60 | 348/239 |
| 2015/0324536 A1* | 11/2015 | Shie | G06F 16/5866 | 715/753 |
| 2015/0363138 A1* | 12/2015 | Inose | G06F 3/121 | 358/1.14 |
| 2016/0022236 A1* | 1/2016 | Ohishi | G06T 7/0016 | 600/431 |
| 2016/0044252 A1* | 2/2016 | Molina | H04N 5/272 | 348/208.6 |
| 2016/0048952 A1* | 2/2016 | Tezaur | G06T 5/004 | 382/255 |
| 2016/0050354 A1* | 2/2016 | Musatenko | H04N 5/2355 | 348/229.1 |
| 2016/0050359 A1* | 2/2016 | Nakata | H01L 27/14621 | 250/201.2 |
| 2016/0069743 A1* | 3/2016 | McQuilkin | G01J 3/2803 | 356/416 |
| 2016/0078322 A1* | 3/2016 | Yamaji | H04N 1/00 | 382/224 |
| 2016/0080626 A1* | 3/2016 | Kovtun | H04N 5/2355 | 348/218.1 |
| 2016/0113626 A1* | 4/2016 | Lee | A61B 5/0035 | 600/440 |
| 2016/0119639 A1* | 4/2016 | Sato | H04N 19/52 | 382/238 |
| 2016/0125630 A1* | 5/2016 | Narahari | H04N 5/235 | 382/167 |
| 2016/0171657 A1* | 6/2016 | Matson | G06T 3/4069 | 382/299 |
| 2016/0171658 A1* | 6/2016 | Matson | G06T 3/4076 | 382/299 |
| 2016/0171715 A1* | 6/2016 | Matson | G06T 3/4069 | 382/103 |
| 2016/0212455 A1* | 7/2016 | Manna | H04N 21/23424 | |
| 2016/0228075 A1* | 8/2016 | Kitamura | A61B 6/12 | |
| 2016/0242743 A1* | 8/2016 | Miyaki | A61B 8/4477 | |
| 2016/0261889 A1* | 9/2016 | Nakagami | H04N 19/70 | |
| 2016/0267704 A1* | 9/2016 | Mistretta | A61B 6/466 | |
| 2016/0277771 A1* | 9/2016 | Nakagami | H04N 19/70 | |
| 2016/0284093 A1* | 9/2016 | Haim | G06T 7/50 | |
| 2016/0301932 A1* | 10/2016 | Kurokawa | H04N 19/44 | |
| 2016/0307331 A1* | 10/2016 | Mollus | G06T 7/344 | |
| 2016/0328828 A1* | 11/2016 | Zhang | G06T 11/60 | |
| 2016/0335752 A1* | 11/2016 | Lim | G06T 7/246 | |
| 2016/0350573 A1* | 12/2016 | Kitchens, II | G06K 9/0002 | |
| 2016/0350940 A1* | 12/2016 | Wang | G06T 7/0012 | |
| 2016/0358335 A1* | 12/2016 | Chukka | G06T 7/90 | |
| 2016/0366335 A1* | 12/2016 | Miyata | H04N 5/23232 | |
| 2016/0373658 A1* | 12/2016 | Ikeda | G06T 3/4069 | |
| 2016/0374635 A1* | 12/2016 | Ning | A61B 6/4241 | 378/5 |
| 2017/0004606 A1* | 1/2017 | Naruse | H04N 1/4092 | |
| 2017/0032527 A1* | 2/2017 | Murthy | H04N 5/33 | |
| 2017/0034496 A1* | 2/2017 | Ishimaru | H04N 1/484 | |
| 2017/0041576 A1* | 2/2017 | Kobayashi | H04N 9/097 | |
| 2017/0052982 A1* | 2/2017 | Sirven | G06F 16/5866 | |
| 2017/0068643 A1* | 3/2017 | Shamir | G06F 40/169 | |
| 2017/0078735 A1* | 3/2017 | Greene | H04N 21/6125 | |
| 2017/0085818 A1* | 3/2017 | Ayers | H04N 5/2628 | |
| 2017/0094326 A1* | 3/2017 | Arimilli | H04N 21/23439 | |
| 2017/0111566 A1* | 4/2017 | Nemoto | G06T 7/20 | |
| 2017/0116512 A1* | 4/2017 | Kurokawa | G06N 3/063 | |
| 2017/0124707 A1* | 5/2017 | Sugiura | G01R 33/48 | |
| 2017/0140250 A1* | 5/2017 | Maloney | G06T 11/60 | |
| 2017/0154420 A1* | 6/2017 | Barnes | G06T 5/003 | |
| 2017/0169567 A1* | 6/2017 | Chefd'hotel | G06K 9/00127 | |
| 2017/0178395 A1* | 6/2017 | Pharr | G06T 15/205 | |
| 2017/0180704 A1* | 6/2017 | Panescu | A61B 34/37 | |
| 2017/0181798 A1* | 6/2017 | Panescu | A61B 34/37 | |
| 2017/0181808 A1* | 6/2017 | Panescu | A61B 34/37 | |
| 2017/0181809 A1* | 6/2017 | Panescu | A61B 8/466 | |
| 2017/0186365 A1* | 6/2017 | Yoneda | H04N 19/10 | |
| 2017/0188011 A1* | 6/2017 | Panescu | H04N 13/275 | |
| 2017/0188986 A1* | 7/2017 | Nakagawa | G06T 19/20 | |

(56) References Cited

U.S. PATENT DOCUMENTS

| | | | |
|---|---|---|---|
| 2017/0200064 A1* | 7/2017 | Reicher | G06K 9/6267 |
| 2017/0206676 A1* | 7/2017 | Nakazato | G06T 11/60 |
| 2017/0208248 A1* | 7/2017 | Mowry | G03B 17/48 |
| 2017/0208334 A1* | 7/2017 | Yoo | H04N 19/136 |
| 2017/0220000 A1* | 8/2017 | Ozcan | G03H 1/0866 |
| 2017/0220716 A1* | 8/2017 | Padoy | A61N 5/1048 |
| 2017/0231478 A1* | 8/2017 | Nemoto | H04N 7/18 345/3.1 |
| 2017/0231586 A1* | 8/2017 | Hirai | A61B 6/0407 378/42 |
| 2017/0248518 A1* | 8/2017 | Nadkarni | G01N 21/4788 |
| 2017/0264773 A1* | 9/2017 | Okamoto | H04N 5/772 |
| 2017/0270346 A1* | 9/2017 | Ascierto | G06K 9/00147 |
| 2017/0270405 A1* | 9/2017 | Kurokawa | G06N 3/0635 |
| 2017/0270666 A1* | 9/2017 | Barnes | G06T 7/12 |
| 2017/0287190 A1* | 10/2017 | Lin | G06T 5/50 |
| 2017/0301094 A1* | 10/2017 | Vignon | G06T 5/20 |
| 2017/0309021 A1* | 10/2017 | Barnes | G06T 7/0012 |
| 2017/0322279 A1* | 11/2017 | Polimeni | G01R 33/4833 |
| 2017/0334225 A1* | 11/2017 | Dunga | G06F 3/1256 |
| 2017/0337336 A1* | 11/2017 | Weidner | G16H 50/20 |
| 2017/0356976 A1* | 12/2017 | Shapiro | A61B 5/7267 |
| 2017/0366785 A1* | 12/2017 | Jacobsen | G06F 3/012 |
| 2018/0028156 A1* | 2/2018 | Matsunaga | A61B 8/5207 |
| 2018/0041673 A1* | 2/2018 | Lee | H04N 5/23293 |
| 2018/0041744 A1* | 2/2018 | Fukuda | G03B 35/10 |
| 2018/0061456 A1* | 3/2018 | Martinez | G06K 9/00744 |
| 2018/0063409 A1* | 3/2018 | Rivard | H04N 5/2258 |
| 2018/0077360 A1* | 3/2018 | Furukawa | G06T 5/20 |
| 2018/0078123 A1* | 3/2018 | Seki | G06T 7/55 |
| 2018/0101359 A1* | 4/2018 | Harada | G06F 7/5443 |
| 2018/0116631 A1* | 5/2018 | Taniguchi | G01S 15/895 |
| 2018/0120553 A1* | 5/2018 | Leshem | G02B 21/34 |
| 2018/0121709 A1* | 5/2018 | Garsha | G06K 9/38 |
| 2018/0137598 A1* | 5/2018 | Spitzer | G06F 3/013 |
| 2018/0137602 A1* | 5/2018 | Spitzer | G02B 27/2228 |
| 2018/0137603 A1* | 5/2018 | Hsiao | G06T 3/4053 |
| 2018/0150962 A1* | 5/2018 | Fletcher | G06T 7/337 |
| 2018/0160058 A1* | 6/2018 | Nakata | H01L 27/14605 |
| 2018/0174340 A1* | 6/2018 | Shah | G06T 11/60 |
| 2018/0183984 A1* | 6/2018 | Fukuda | G06T 1/0007 |
| 2018/0197303 A1* | 7/2018 | Jordan | G06T 7/0014 |
| 2018/0205898 A1* | 7/2018 | Johansson | H04N 5/365 |
| 2018/0205909 A1* | 7/2018 | Staranowicz | H04N 7/014 |
| 2018/0206820 A1* | 7/2018 | Anand | A61B 8/4405 |
| 2018/0217743 A1* | 8/2018 | Ishida | G06F 3/04847 |
| 2018/0225810 A1* | 8/2018 | Kajimura | G06T 7/248 |
| 2018/0225866 A1* | 8/2018 | Zhang | G06T 7/593 |
| 2018/0260649 A1* | 9/2018 | Kadambe | G06K 9/3241 |
| 2018/0260669 A1* | 9/2018 | Konishi | G06T 1/0014 |
| 2018/0300904 A1* | 10/2018 | Kawakami | G06T 9/00 |
| 2018/0302650 A1* | 10/2018 | Kawamura | H04N 19/63 |
| 2018/0308217 A1* | 10/2018 | Kurita | B60R 11/02 |
| 2018/0309940 A1* | 10/2018 | Okada | G06T 5/007 |
| 2018/0315225 A1* | 11/2018 | Zhang | G06T 5/00 |
| 2018/0322614 A1* | 11/2018 | Petrova | G06T 5/20 |
| 2018/0322628 A1* | 11/2018 | Schroecker | A61B 8/488 |
| 2018/0322632 A1* | 11/2018 | Barnes | G06T 7/11 |
| 2018/0324383 A1* | 11/2018 | Kaneko | H04N 5/247 |
| 2018/0326223 A1* | 11/2018 | Willcut | A61N 5/1037 |
| 2018/0329609 A1* | 11/2018 | De Swarte | G06F 3/04842 |
| 2018/0330160 A1* | 11/2018 | Yamamoto | G06K 9/6202 |
| 2018/0338086 A1* | 11/2018 | Marineau-Mes | G06T 5/50 |
| 2018/0357750 A1* | 12/2018 | Chen | G06T 3/4038 |
| 2018/0360313 A1* | 12/2018 | Zhang | A61B 5/004 |
| 2018/0365461 A1* | 12/2018 | Wang | G06K 7/1417 |
| 2019/0000408 A1* | 1/2019 | Kesner | A61B 8/5284 |
| 2019/0019279 A1* | 1/2019 | Kumar | G06T 3/4069 |
| 2019/0026603 A1* | 1/2019 | Li | G06K 9/00771 |
| 2019/0046020 A1* | 2/2019 | Shiraki | A61B 1/00 |
| 2019/0051022 A1* | 2/2019 | Kikuchi | A61B 1/04 |
| 2019/0068929 A1* | 2/2019 | Sato | H04N 9/0451 |
| 2019/0073510 A1* | 3/2019 | West | G06K 9/0014 |
| 2019/0073792 A1* | 3/2019 | Fletcher | G06T 7/73 |
| 2019/0079004 A1* | 3/2019 | Ulanch | G01N 21/274 |
| 2019/0080498 A1* | 3/2019 | Horie | H04N 5/272 |
| 2019/0099058 A1* | 4/2019 | Takeda | A61B 1/00009 |
| 2019/0107989 A1* | 4/2019 | Mizobe | G06F 3/1446 |
| 2019/0122633 A1* | 4/2019 | Pan | G09G 5/005 |
| 2019/0130192 A1* | 5/2019 | Kauffmann | G06K 9/00765 |
| 2019/0130528 A1* | 5/2019 | Kim | G06T 3/4007 |
| 2019/0132528 A1* | 5/2019 | Nashizawa | G06T 7/32 |
| 2019/0139472 A1* | 5/2019 | Liu | G02B 30/27 |
| 2019/0149728 A1* | 5/2019 | Kajimura | H04N 5/23299 348/222.1 |
| 2019/0156483 A1* | 5/2019 | Kono | A61B 1/04 |
| 2019/0172182 A1* | 6/2019 | Onzon | G06T 5/10 |
| 2019/0174992 A1* | 6/2019 | Fujii | A61B 1/00029 |
| 2019/0188827 A1* | 6/2019 | Mitani | H04N 5/23229 |
| 2019/0191082 A1* | 6/2019 | Uehara | H04N 5/23238 |
| 2019/0197667 A1* | 6/2019 | Paluri | G06K 9/4652 |
| 2019/0197712 A1* | 6/2019 | Talbert | G01J 3/10 |
| 2019/0215420 A1* | 7/2019 | Kaneko | H04N 5/225 |
| 2019/0223841 A1* | 7/2019 | Miyazawa | A61B 8/54 |
| 2019/0230281 A1* | 7/2019 | Ohba | H04N 5/23232 |
| 2019/0254759 A1* | 8/2019 | Azizian | A61B 34/25 |
| 2019/0259139 A1* | 8/2019 | Ichihashi | G06T 7/579 |
| 2019/0278793 A1* | 9/2019 | Henry | G06F 16/24578 |
| 2019/0302211 A1* | 10/2019 | Cai | G06T 7/20 |
| 2019/0306471 A1* | 10/2019 | Otsuki | H01L 27/14605 |
| 2019/0311461 A1* | 10/2019 | Mercer | G06T 5/50 |
| 2019/0347768 A1* | 11/2019 | Lelescu | G06T 3/4053 |
| 2019/0378257 A1* | 12/2019 | Fan | H04N 9/67 |
| 2019/0378258 A1* | 12/2019 | Fan | H04N 5/33 |
| 2020/0045227 A1* | 2/2020 | Jiang | H04N 5/23232 |
| 2020/0075154 A1* | 3/2020 | Akahori | G16H 50/20 |
| 2020/0082151 A1* | 3/2020 | Huang | G06K 9/6289 |
| 2020/0090305 A1* | 3/2020 | El-Khamy | G06N 3/0454 |
| 2020/0090330 A1* | 3/2020 | Chefd'hotel | G06T 7/0012 |
| 2020/0097719 A1* | 3/2020 | Lodhia | G06F 40/186 |
| 2020/0104859 A1* | 4/2020 | Eklund | G06Q 30/02 |
| 2020/0105004 A1* | 4/2020 | Haim | G06T 5/50 |
| 2020/0118250 A1* | 4/2020 | Takahama | G06T 5/002 |
| 2020/0120271 A1* | 4/2020 | Furukawa | H04N 5/349 |
| 2020/0120272 A1* | 4/2020 | Furukawa | G06T 7/32 |
| 2020/0125245 A1* | 4/2020 | Osada | G06F 3/04847 |
| 2020/0193585 A1* | 6/2020 | Ikegami | G06T 5/003 |
| 2020/0202518 A1* | 6/2020 | Vignon | G06T 7/73 |
| 2020/0250794 A1* | 8/2020 | Zimmer | G06T 3/4076 |
| 2020/0264423 A1* | 8/2020 | Oshima | G02B 21/244 |
| 2020/0310100 A1* | 10/2020 | Ozcan | G03H 1/0866 |
| 2020/0402209 A1* | 12/2020 | Talbert | G06T 7/223 |
| 2021/0004934 A1* | 1/2021 | Bae | G06K 9/6268 |
| 2021/0015460 A1* | 1/2021 | Miyachi | A61B 8/5246 |
| 2021/0035299 A1* | 2/2021 | Ikegami | G06T 7/337 |
| 2021/0059644 A1* | 3/2021 | Liu | A61B 8/5246 |
| 2021/0110514 A1* | 4/2021 | Anger | G06K 9/6289 |

FOREIGN PATENT DOCUMENTS

| | | |
|---|---|---|
| JP | 2013-88676 | 5/2013 |
| JP | 2014-206926 A | 10/2014 |
| WO | WO 2006/064751 A1 | 6/2006 |

OTHER PUBLICATIONS

International Search Report dated Feb. 21, 2017, in PCT/JP2016/084380 filed Nov. 21, 2016.

Hanoch, U. et al., "Improved Resolution from Subpixel Shifted Pictures", CVGIP Graphical Models and Image Processing, vol. 54, No. 2, (1992), pp. 181-186, XP 000281942.

Ng, M. et al.. "Preconditioned Interative Methods for Super-Resolution Image Reconstruction with Multisensors", Proceedings of SPIE. vol. 4116, (2000), pp. 396-405. XP 008008185.

Peled, S. et al., "Superresolution in MRI: Application to Human White Matter Fiber Tract Visualization by Diffusion Tensor Imaging" , Magnetic Resonance in Medicine, vol. 45, No. 1, (2001), pp. 29-35, XP000981008.

Peleg, S. et al., "Improving Image Resolution Using Subpixel Motion", Pattern Recognition Letters, vol. 5, No. 3, (1987), pp. 223-226, XP000005461.

(56) References Cited

OTHER PUBLICATIONS

Jacquemod, G. et al., "Image Resolution Enhancement Using Subpixel Camera Displacement", Signal Processing. vol. 26, No. 1, (1992), pp. 139-146. XP002351548.
Anonymous, "Phase", Britannica Concise Encyclopaedia, Inc., (2006), 3 pages, XP055343482.
Japanese Office Action dated Sep. 17, 2019, issued in corresponding Japanese Patent Application No. 2015-234744.

* cited by examiner

SURGERY CONTROL APPARATUS, SURGERY CONTROL METHOD, PROGRAM, AND SURGERY SYSTEM

TECHNICAL FIELD

The present disclosure relates to a surgery control apparatus, a surgery control method, a program, and a surgery system, and particularly to a surgery control apparatus, a surgery control method, a program, and a surgery system which make it possible to sufficiently improve quality of a high resolution image generated by a pixel shift.

CROSS REFERENCE TO RELATED APPLICATIONS

This application claims the benefit of Japanese Priority Patent Application JP 2015-234744 filed Dec. 1, 2015, the entire contents of which are incorporated herein by reference.

BACKGROUND ART

In these days, on a medical site, an endoscopic surgery in which a surgery is conducted while taking images of an operative field with an endoscope is conducted instead of a laparotomy in the past.

On the other hand, performing a return process is conceived in which a high resolution image is generated by using such a pixel shift technique that a plurality of images having different phases are taken. However, the phases of images may be deviated from ideal values due to a change with time. In this case, quality of a high resolution image to be generated may be deteriorated.

In view of this, improving the quality of a high resolution image by detecting an amount of deviation of a phase from an ideal value and generating a high resolution image while taking the detected amount of deviation into consideration has been conceived (see, for example, Patent Literature 1 and 2).

CITATION LIST

Patent Literature

PTL 1: International Publication WO 2006/064751
PTL 2: Japanese Patent Application Laid-open No. 2013-88676

SUMMARY OF INVENTION

Technical Problem

However, in Patent Literature 1 and 2, in the case where detection accuracy of the amount of deviation from the ideal value of the shift is low, quality of a high resolution image is not sufficiently improved.

In view of the circumstances as described above, the present disclosure has been made and makes it possible to sufficiently improve the quality of a high resolution image generated by a pixel shift.

Solution to Problem

According to an embodiment of the present disclosure, there is provided a medical system, including a medical imaging device and circuitry configured to: obtain a plurality of first images each having a different phase from the medical imaging device, combine each of the plurality of first images a plurality of times to generate a plurality of second images, wherein each time of the plurality of times that the plurality of first images are combined, a different candidate process is used in the combining, and select one image from the plurality of second images as an output image for display, wherein the selected one image is higher quality than any one of the plurality of first images.

According to an embodiment of the present disclosure, there is provided a medical image processing apparatus, including circuitry that obtains a plurality of first images each having a different phase from a medical imaging device, combines each of the plurality of first images a plurality of times to generate a plurality of second images, wherein each time of the plurality of times that the plurality of first images are combined, a different candidate process is used in the combining, and selects one image from the plurality of second images as an output image for display, wherein the selected one image is higher quality than any one of the plurality of first images.

According to an embodiment of the present disclosure, there is provided a medical system, including a medical imaging device, and circuitry that obtains data associated with a plurality of first images each having a different phase from the medical imaging device, processes the data associated with each of the plurality of first images a plurality of times to generate a plurality of second images, wherein each time of the plurality of times that the data associated with the plurality of first images are processed, a different candidate process is used in the processing, and selects one image from the plurality of second images as an output image for display, wherein the selected one image is higher quality than any one of the plurality of first images.

According to an embodiment of the present disclosure, there is provided a medical image processing method, including obtaining a plurality of first images each having a different phase from a medical imaging device, combining each of the plurality of first images a plurality of times to generate a plurality of second images, wherein each time of the plurality of times that the plurality of first images are combined, a different candidate process is used in the combining, and selecting one image from the plurality of second images as an output image for display, wherein the selected one image is higher quality than any one of the plurality of first images.

Advantageous Effects of Invention

According to at least one embodiment of the present disclosure, by performing the plurality of kinds of processes for the plurality of images having different phases taken by the surgery image pickup apparatus, a plurality of high resolution images having a resolution higher than the plurality of images, and on the basis of the generated plurality of high resolution images, one of the plurality of kinds of processes is selected.

According to at least one embodiment of the present disclosure, it is possible to perform image processing. Further, according to the first and second embodiments of the present disclosure, it is possible to sufficiently improve the quality of the high resolution image generated by the pixel shift.

It should be noted that the effect disclosed herein is not necessarily limited, and any effect described in the present disclosure may be obtained.

DESCRIPTION OF EMBODIMENTS

Figure 1:
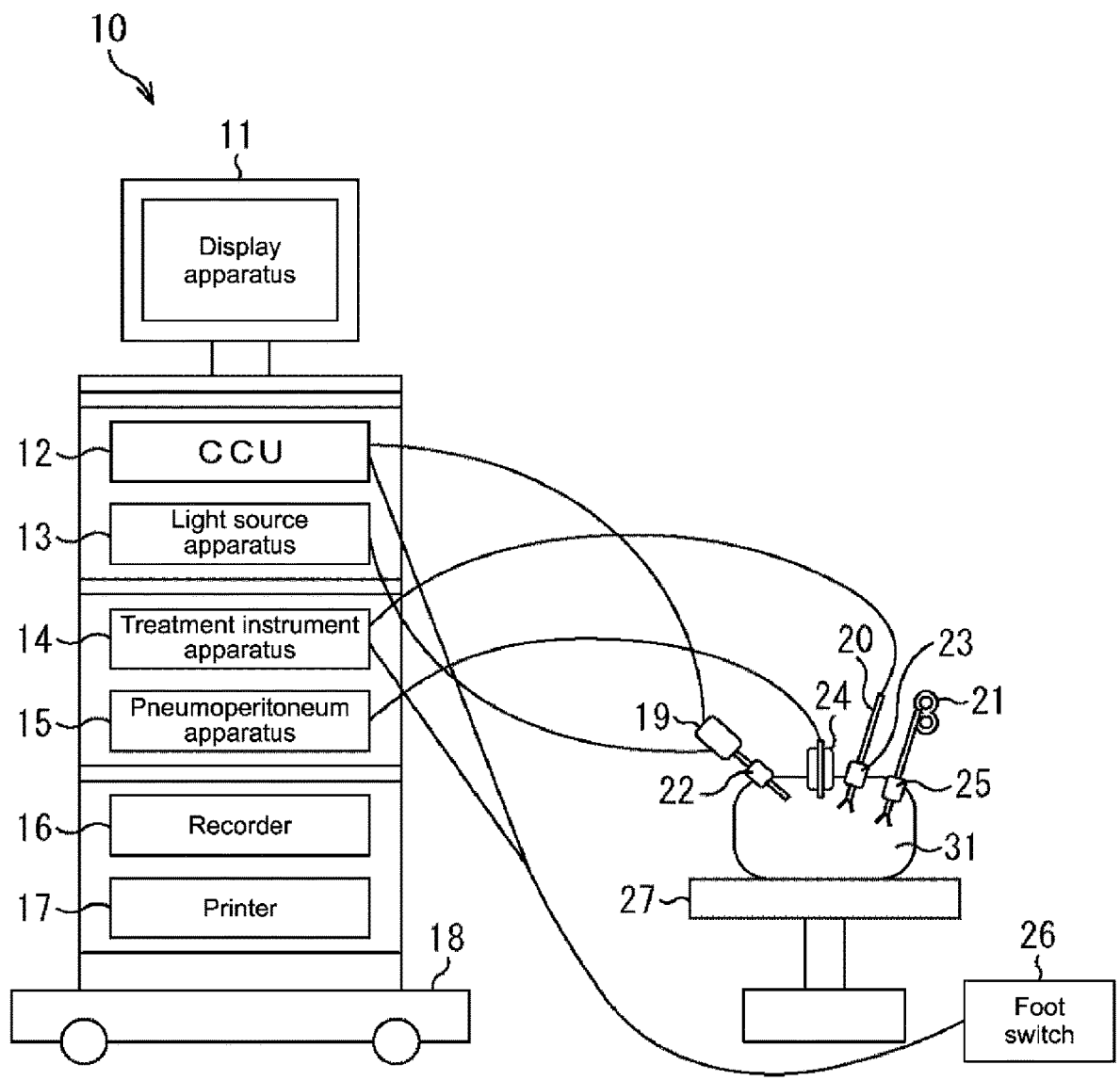
FIG. 1 is a diagram showing a configuration example of a first embodiment of an endoscopic surgery system to which the present disclosure is applied.

Hereinafter, modes for carrying out the present disclosure (hereinafter, referred to as embodiments) will be described. It should be noted that, description will be given in the following order.
1. First embodiment: endoscopic surgery system (FIG. 1 to FIG. 11)
2. Second embodiment: endoscopic surgery system (FIG. 12)
3. Third embodiment: endoscopic surgery system (FIG. 13)

First Embodiment (Configuration Example of First Embodiment of Endoscopic Surgery System)

An endoscopic surgery system 10 is provided with a cart 18 on which a display apparatus 11, a camera control unit (CCU) 12, a light source apparatus 13, a treatment instrument apparatus 14, a pneumoperitoneum apparatus 15, a recorder 16, and a printer 17 are mounted. Further, the endoscopic surgery system 10 has an endoscope (laparoscope) 19, an energy treatment instrument 20, an extractor 21, trocars 22 to 25, a foot switch 26, and a patient bed 27. The endoscopic surgery system 10 is disposed in a surgery room, for example, and assists an operator who conducts an endoscopic surgery for a diseased part included in an abdominal portion 31 of a patient lying on the patient bed 27.

Specifically, the display apparatus 11 of the endoscopic surgery system 10 is configured by an installation type 2D display, a head mounted display, or the like. The display apparatus 11 displays an image or the like supplied from the CCU 12.

The CCU 12 is connected with the endoscope 19 via a camera cable. It should be noted that the CCU 12 may be wirelessly connected with the endoscope 19. The CCU 12 performs various processes on the basis of operation signals supplied from the foot switch 26.

Further, the CCU 12 receives, via the camera cable, three HD (High Definition) images having different phases obtained as a result of a pixel shift by the endoscope 19. The CCU 12 has an operation button (not shown). In the case where the CCU 12 is used in the endoscopic surgery system 10, an operator or the like operates the operation button (not shown) held by the CCU 12 and sets an operation mode of the CCU 12 to a normal mode.

In the case where the operation mode is the normal mode, the CCU 12 generates a 4 k-resolution image with the use of the received HD images by a predetermined return process. Then, the CCU 12 supplies the generated 4 k-resolution image (hereinafter, referred to as high resolution image) to the display apparatus 11. The 4 k resolution refers to a horizontal resolution of approximately 4000, for example, 3860 or 4096. When necessary, the CCU 12 supplies the high resolution image to the recorder 16 or the printer 17.

The light source apparatus 13 is connected with the endoscope 19 via a light guide cable. The light source apparatus 13 switches and emits light with various wavelengths to the endoscope 19.

The treatment instrument apparatus 14 is a high frequency output apparatus, and is connected with the energy treatment instrument 20 and the foot switch 26 via a cable. The treatment instrument apparatus 14 outputs high frequency current to the energy treatment instrument 20 in accordance with an operation signal supplied from the foot switch 26.

The pneumoperitoneum apparatus 15 is provided with an air sending means and an air intake means, and sends or takes in air to or from the inside of the abdominal portion 31 through a hole of the trocar 24 as an opening instrument attached to an abdominal wall of the abdominal portion 31.

The recorder 16 records an image supplied from the CCU 12. The printer 17 prints the image supplied from the CCU.

The endoscope 19 (surgical image pickup apparatus) is constituted of an image pickup unit and an optical system such as an illumination lens. The endoscope 19 is inserted into the inside of the abdominal portion 31 to be subjected to a surgery from a hole of the trocar 22 attached to the abdominal wall of the abdominal portion 31. The illumination lens of the endoscope 19 applies light emitted from the light source apparatus 13 to the inside of the abdominal portion 31.

The image pickup unit is a three-plate type image pickup unit with three image pickup surfaces having sensitivities with respect to light of red, green, and blue. It should be noted that, hereinafter, the image pickup surfaces having the sensitivities with respect to light of red, green, and blue are referred to as a red image pickup surface, a green image pickup surface, and a blue image pickup surface, respectively. The phase of the green image pickup surface is different from the phase of the red image pickup surface and the blue image pickup surface.

The image pickup unit performs image taking on the green image pickup surface, the red image pickup surface, and the blue image pickup surface at the same time, with the result that the pixel shift is carried out. Thus, the image pickup unit obtains a green HD image of the inside of the abdominal portion 31 and red and blue HD images thereof with a different phase therefrom. The endoscope 19 supplies the three HD images thus obtained to the CCU 12 via the camera cable.

The energy treatment instrument 20 is configured by an electrical scalpel or the like. The energy treatment instrument 20 is inserted into the inside of the abdominal portion 31 from a hole of the trocar 23 attached to the abdominal wall of the abdominal portion 31. The energy treatment instrument 20 denatures or cuts the inside of the abdominal portion 31 with the use of electrical heat generated from high frequency current supplied from the treatment instrument apparatus 14.

The extractor 21 is inserted into the inside of the abdominal portion 31 from a hole of the trocar 25 attached to the abdominal wall of the abdominal portion 31. The extractor 21 holds the inside of the abdominal portion 31. The endoscope 19, the energy treatment instrument 20, and the extractor 21 are held by the operator, an assistant, a scopist, a robot, or the like.

The foot switch 26 receives an operation with a foot of the operator, the assistant, or the like. The foot switch 26 supplies an operation signal that indicates the received operation to the CCU 12 or the treatment instrument apparatus 14.

By using the endoscopic surgery system 10 configured as described above, the operator can resect a diseased part in the abdominal portion 31 without conducting such a laparotomy that the abdominal wall is cut to open an abdominal cavity.

In the endoscopic surgery system 10 as described above, the phases of images obtained by the pixel shift may be deviated from ideal values in some cases due to a change with time, heat at a time of sterilization treatment, or the like. In this case, it may be impossible to generate a high resolution image having high quality by the return process optimal in the case where the phases are the ideal values. Thus, the operator or the like has to periodically optimize the return process.

(Configuration Example of Optimization System)

Figure 2:
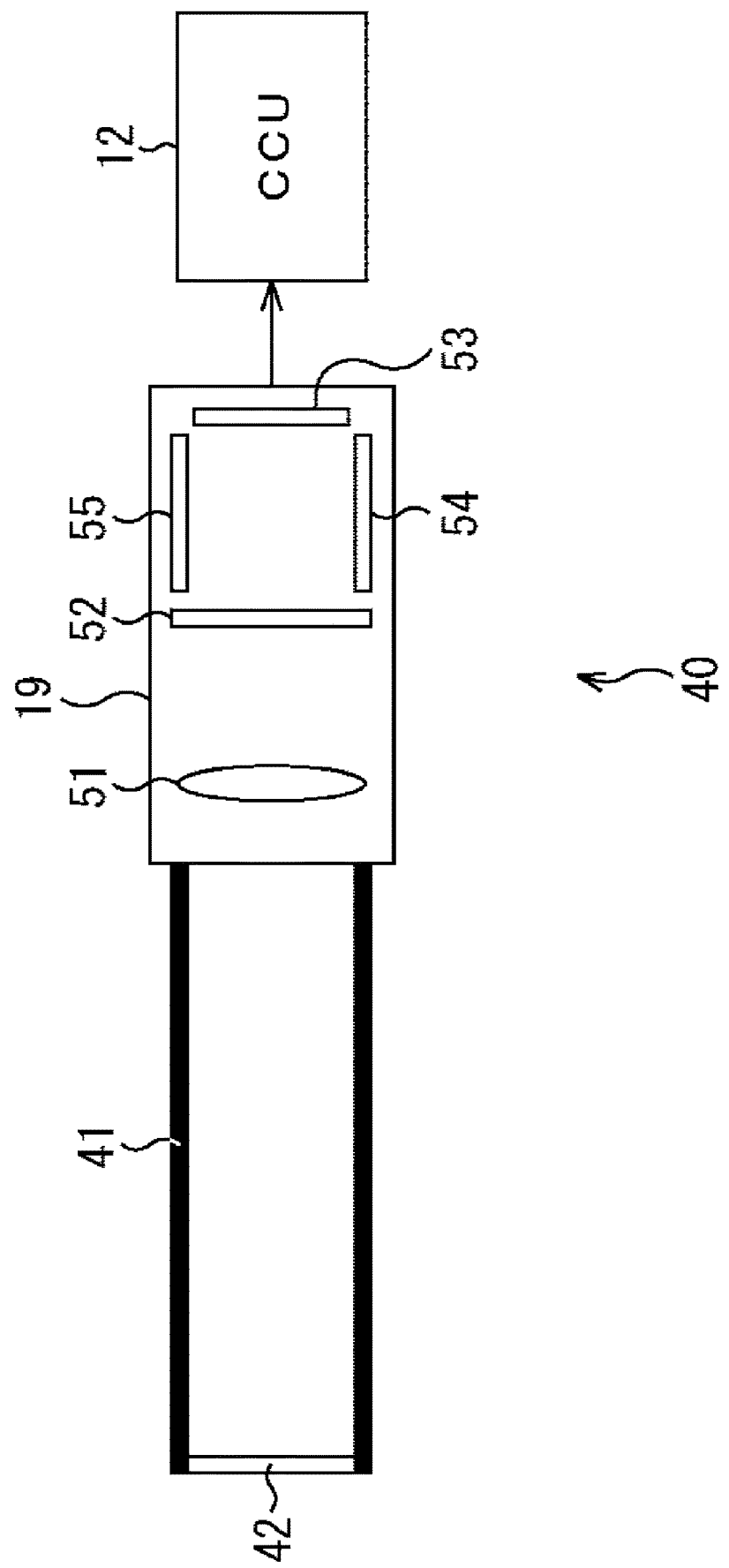
FIG. 2 is a diagram showing a configuration example of an optimization system.

FIG. 2 is a diagram showing a configuration example of an optimization system used for optimization of the return process in the CCU 12 shown in FIG. 1.

An optimization system 40 (surgery system) shown in FIG. 2 is constituted of the CCU 12, the endoscope 19, a jig 41, and a chart 42.

When performing optimization of the return process, the operator or the like attaches the jig 41 holding the chart 42 to the endoscope 19 to which the CCU 12 is connected. Then, the operator or the like operates the operation button (not shown) of the CCU 12, thereby setting the operation mode to an optimization mode.

The jig 41 fixes a positional relationship between the endoscope 19 and the chart 42.

The endoscope 19 performs the pixel shift with the chart 42 as a subject. Specifically, light from the chart 42 passes through a lens 51 of the optical system of the endoscope 19 and is separated into a red component, a green component, and a blue component by a prism 52. The separated red component is collected on a red image pickup surface 53 of the image pickup unit, and the red image pickup surface 53 obtains an HD image of red (hereinafter, referred to as red image). Similarly, the green component is collected on a green image pickup surface 54, and the green image pickup surface 54 obtains an HD image of green (hereinafter, referred to as green image) with a different phase from the red image. Further, the blue component is collected on a blue image pickup surface 55, and the blue image pickup surface 55 obtains an HD image of blue (hereinafter, referred to as blue image) with the same phase as the red image. The endoscope 19 transmits the red image, the green image, and the blue image to the CCU 12 via the camera cable or the like.

In the case where the operation mode is the optimization mode, the CCU 12 uses the red image, the green image, and the blue image transmitted from the endoscope 19, to generate a high resolution image by a plurality of kinds of return processes. On the basis of the high resolution image generated by the plurality of kinds of return processes and a reference image as an ideal high resolution image of the chart 42, the CCU 12 selects, as an optimal return process, one from among the plurality of kinds of return processes. The selected optimal return process is performed in the normal mode.

(Example of Design of Chart)

Figure 3:
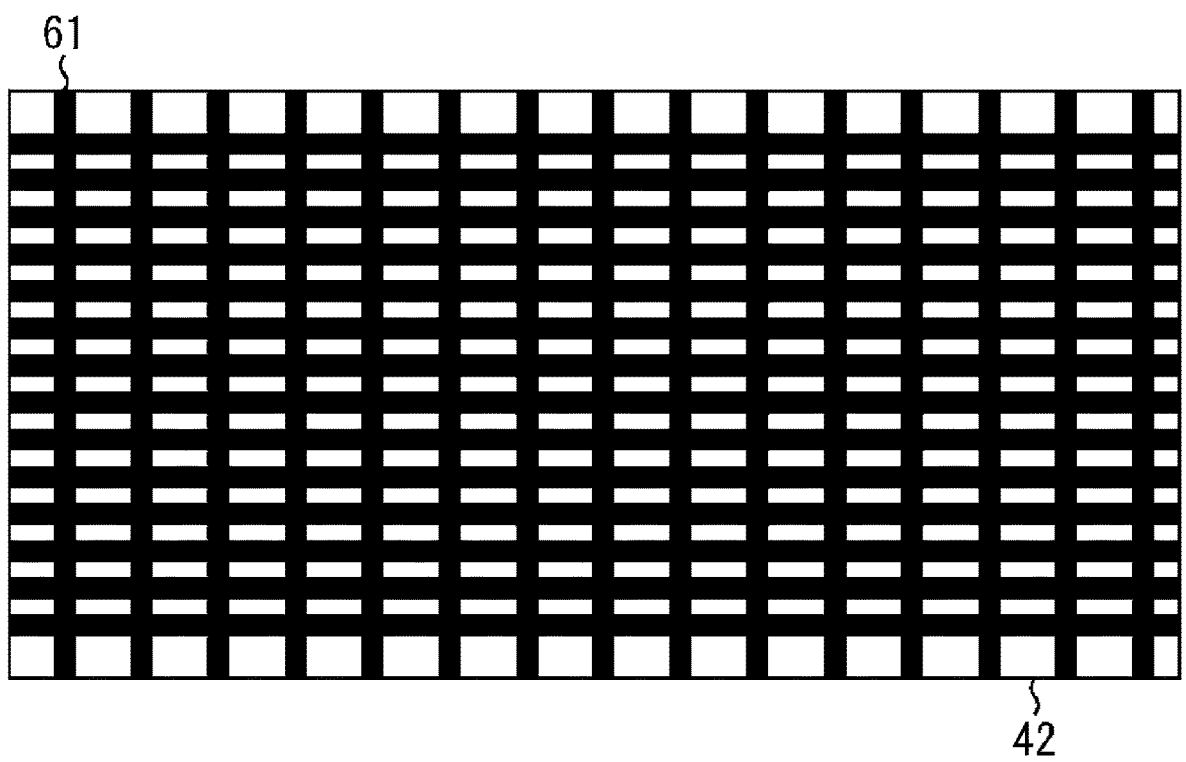
FIG. 3 is a diagram showing an example of a pattern of a chart.
Figure 4:
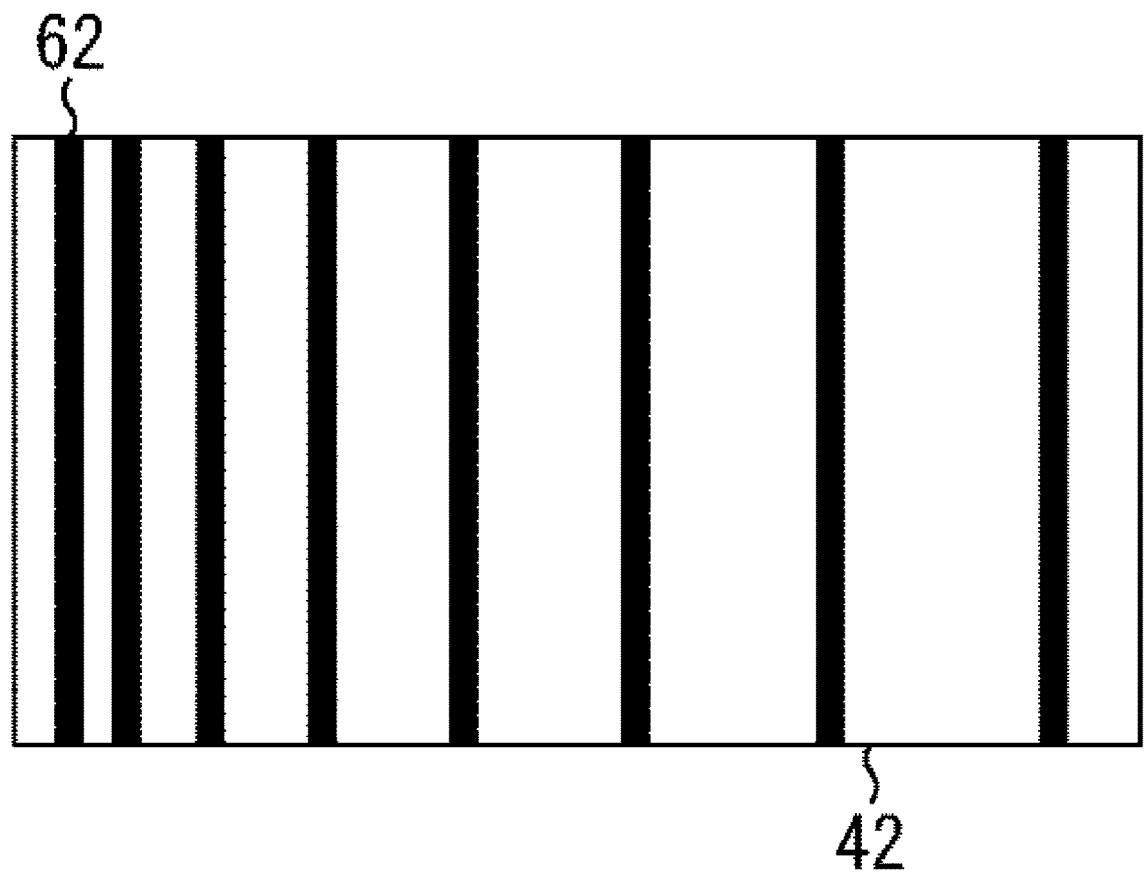
FIG. 4 is a diagram showing an example of a pattern of the chart.
Figure 5:
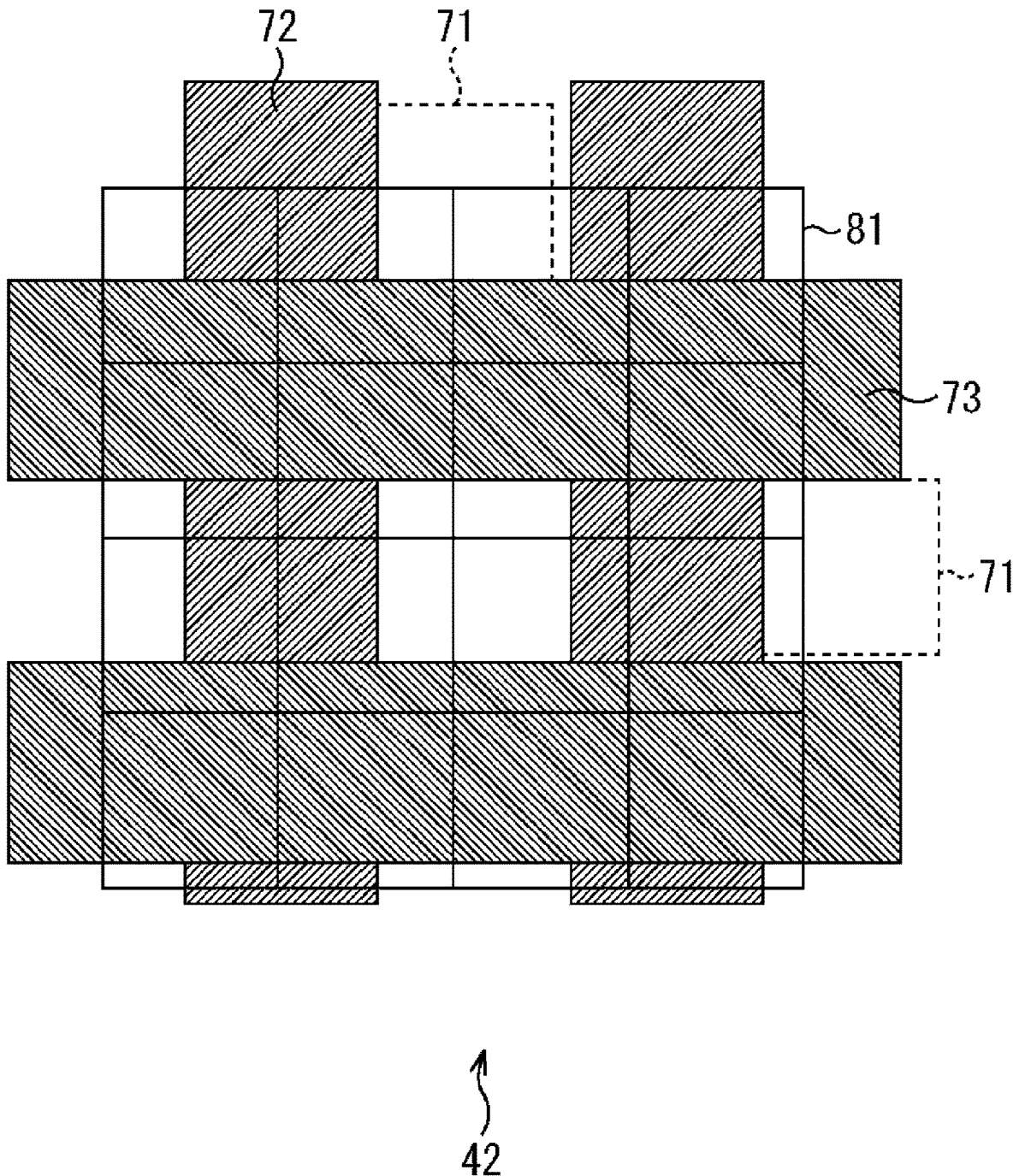
FIG. 5 is a diagram showing an example of a pattern of the chart.

FIGS. 3 to 5 are diagrams showing examples of patterns of the chart 42.

The pattern of the chart 42 may be lattice lines 61 as shown in FIG. 3 or may be vertical lines 62 arranged at different intervals as shown in FIG. 4. Further, as shown in FIG. 5, the pattern of the chart 42 may be vertical lines 72 and horizontal lines 73, the vertical lines 72 being arranged at intervals longer than a horizontal length of a size 71 of at least one pixel of the red image pickup surface, the green image pickup surface, and the blue image pickup surface, the horizontal lines 73 being arranged at intervals longer than a vertical length thereof.

In the case where the pattern of the chart 42 is as shown in FIG. 5, the jig 41 fixes the chart 42 and the endoscope 19 in such a manner that an image pickup area 81 of 4×4 pixels of the red image pickup surface 53 includes boundaries of the vertical lines 72 and the horizontal lines 73 on the chart 42.

It should be noted that the pattern of the chart 42 is not limited to the patterns shown in FIGS. 3 to 5 and may be any pattern as long as the high resolution image generated by the CCU 12 is affected by deviation amounts from the ideal values of the phases of the red image, the green image, and the blue image. In addition, the operator or the like may cause the jig 41 to hold a plurality of charts 42 in order.

(Configuration Example of Hardware of CCU)

Figure 6:
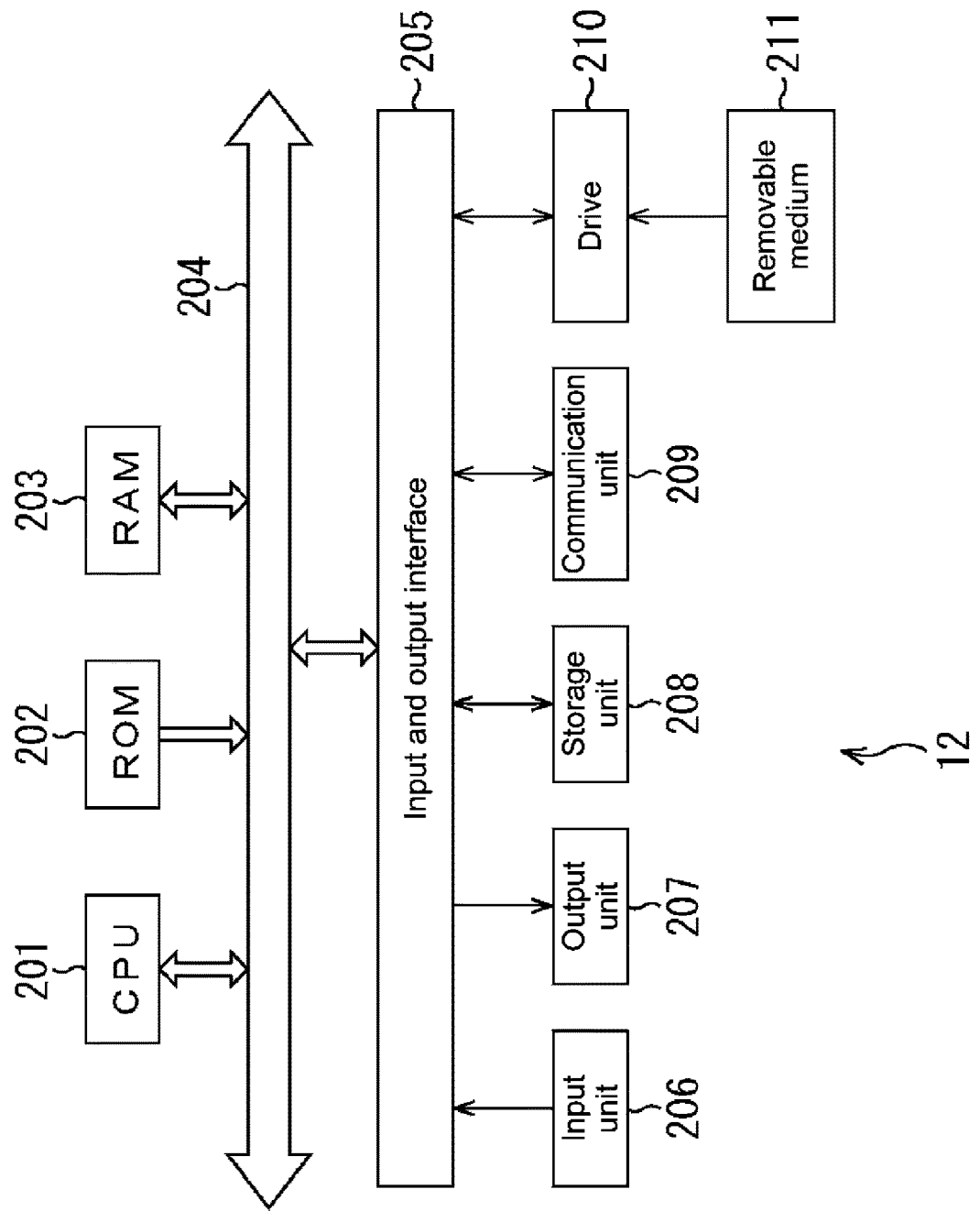
FIG. 6 is a block diagram showing a configuration example of hardware of a CCU.

FIG. 6 is a block diagram showing a configuration example of hardware of the CCU 12.

In the CCU 12, a central processing unit (CPU) 201, a read only memory (ROM) 202, and a random access memory (RAM) 203 are connected with one another via a bus 204.

To the bus 204, an input and output interface 205 is further connected. To the input and output interface 205, an input unit 206, an output unit 207, a storage unit 208, a communication unit 209, and a drive 210 are connected.

The input unit 206 includes an operation button, a keyboard, a mouse, a microphone, or the like. The output unit 207 includes a display, a speaker, or the like. The storage unit 208 includes a hard disk, a nonvolatile memory, or the like. The communication unit 209 includes a network interface or the like. The communication unit 209 performs communication with the display apparatus 11, the endoscope 19, the recorder 16, the printer 17, and the foot switch 26. The drive 210 drives a removable medium 211 such as a magnetic disk, an optical disc, a magneto-optical disk, and a semiconductor memory.

In the CCU 12 configured as described above, for example, the CPU 201 loads a program stored in the storage unit 208 into the RAM 203 through the input and output interface 205 and the bus 204 and executes the program, with the result that a return control process or the like is performed. The return control process refers to a process of performing optimization of the return process or performing the return process in accordance with the operation mode.

The program executed by the CCU 12 (CPU 201) can be recorded in the removable medium 211 as a package medium or the like and provided, for example. Further, the program can be provided via a wired or wireless transmission medium such as a local area network, the Internet, and digital satellite broadcasting.

In the CCU 12, the program can be installed into the storage unit 208 by loading the removable medium 211 to the drive 210 through the input and output interface 205. Further, via the wired or wireless transmission medium, the program can be received by the communication unit 209 and installed into the storage unit 208. In addition, the program can be installed in advance into the ROM 202 or the storage unit 208.

It should be noted that, the program executed by the CCU 12 may be a program, processing of which is executed on a time-series basis in order of description in this specification, or may be a program, processing of which is executed in parallel or at necessary timing, for example, when called.

(Functional Configuration Example of CCU)

Figure 7:
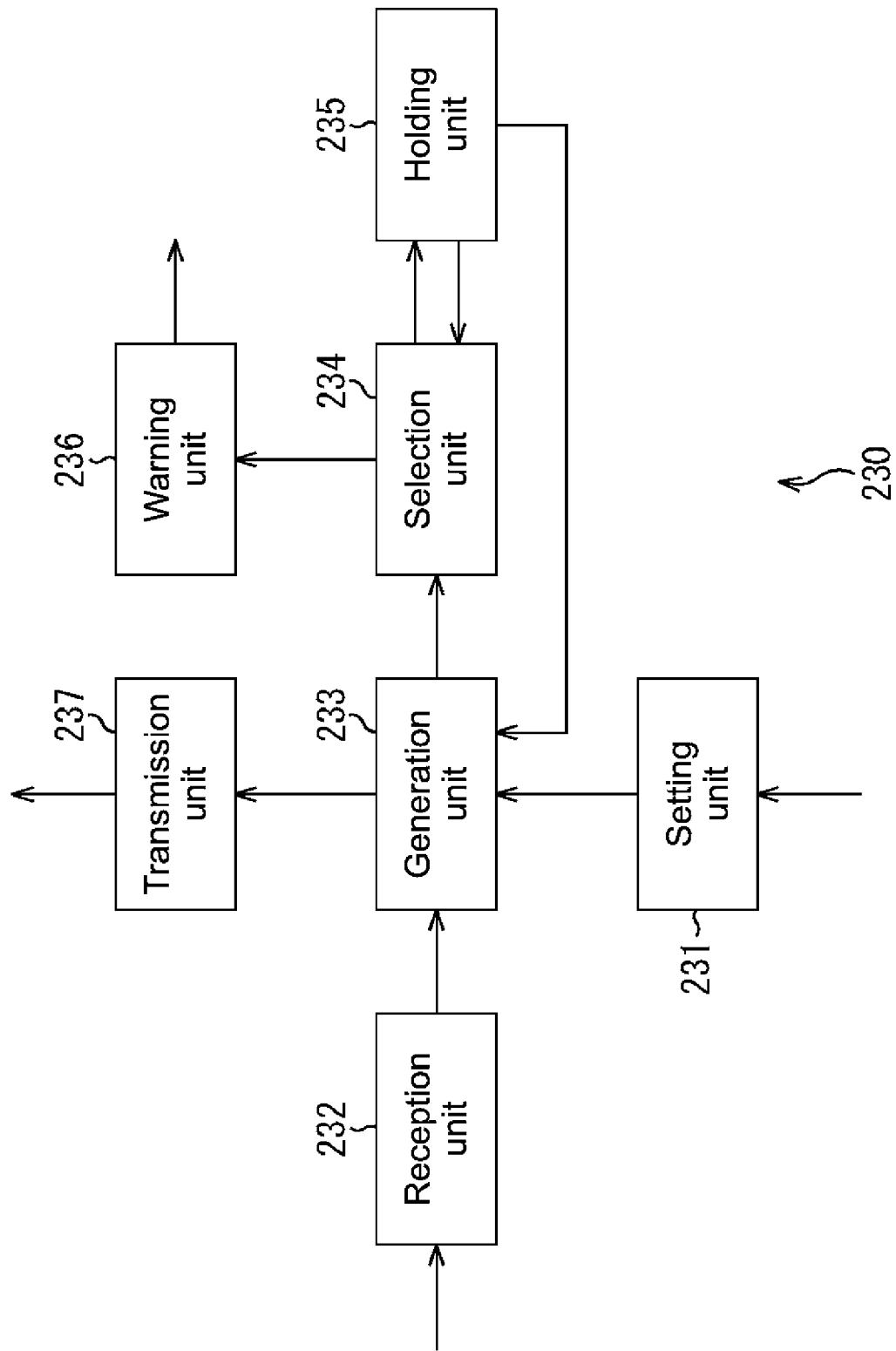
FIG. 7 is a block diagram showing an example of a functional configuration of a return control processing unit.

FIG. 7 is a block diagram showing a functional configuration example of a return control processing unit that performs a return control process achieved by the CCU 12 shown in FIG. 6.

A return control processing unit 230 shown in FIG. 7 is constituted of a setting unit 231, a reception unit 232, a generation unit 233, a selection unit 234, a holding unit 235, a warning unit 236, and a transmission unit 237. The setting unit 231, the generation unit 233, and the selection unit 234 are achieved by the CPU 201 shown in FIG. 6, for example, and the reception unit 232 and the transmission unit 237 are achieved by the communication unit, for example. Further, the holding unit 235 is achieved by the storage unit 208, for example, and the warning unit 236 is achieved by the output unit 207, for example.

The setting unit 231 of the return control processing unit 230 sets, in accordance with an operation of the input unit 206 by the operator or the like, the operation mode to a normal mode or an optimization mode. Specifically, when the CCU 12 is used in the endoscopic surgery system 10, the operator or the like operates the input unit 206 to give an instruction of setting to the normal mode, and the setting unit 231 sets the operation mode to the normal mode in accordance with this instruction.

On the other hand, when the CCU 12 is used in the optimization system 40, the operator or the like operates the input unit 206 to give an instruction of setting to the optimization mode, and the setting unit 231 sets the operation mode to the optimization mode in accordance with this instruction. The setting unit 231 supplies the set operation mode to the generation unit 233.

The reception unit 232 receives the red image, the green image, and the blue image transmitted from the endoscope 19 and supplies the images to the generation unit 233.

In the case where the operation mode supplied from the setting unit 231 is the normal mode, the generation unit 233 reads process specifying information to specify the return process from the holding unit 235. Then, the generation unit 233 generates a high resolution image by using the red image, the green image, and the blue image supplied from the reception unit 232 by the return process specified on the basis of the read process specifying information. The generation unit 233 supplies the generated high resolution image to the transmission unit 237.

On the other hand, in the case where the operation mode supplied from the setting unit 231 is the optimization mode, the generation unit 233 generates high resolution images by using the red image, the green image, and the blue image supplied from the reception unit 232 by the plurality of kinds of return processes as candidates of the return process. The return process candidates are, for example, return processes optimal in the case where the deviation amounts from the ideal values of the phases of the red image, the green image, and the blue image are predetermined values. The generation unit 233 associates the plurality of generated high resolution images with the process specifying information of the return process candidates at the time of the generation of the high resolution images, and supplies the images associated with the information to the selection unit 234.

The selection unit 234 reads a reference image from the holding unit 235. The selection unit 234 obtains a difference between each of the plurality of high resolution images supplied from the generation unit 233 and the reference image. The selection unit 234 selects, from among the return process candidates, one corresponding to the high resolution image having the smallest difference from the reference image as the optimal return process. The selection unit 234 supplies the process specifying information of the optimal return process to the holding unit 235.

Further, the selection unit 234 recognizes the deviation amounts from the ideal values of the phases of the red image, the green image, and the blue image corresponding to the optimal return process. In the case where the recognized deviation amounts exceed a threshold value, the selection unit 234 determines that it is necessary to exchange the endoscope 19, and instructs the warning unit 236 to give a warning.

The holding unit 235 holds the process specifying information supplied from the selection unit 234. Further, the holding unit 235 holds the reference image. On the basis of the instruction from the selection unit 234, the warning unit 236 outputs a warning to urge the endoscope 19 to be exchanged. Specifically, in accordance with the instruction from the selection unit 234, for example, the warning unit 236 controls a display (display unit) of the output unit 207, and causes a warning screen to urge the endoscope 19 to be exchanged to be displayed on the display. It should be noted that, the method of outputting the warning is not limited to displaying the warning screen, and may be lighting a warning lamp of the output unit 207, outputting warning sound or the like from a speaker of the output unit 207, or the like.

The transmission unit 237 transmits the high resolution image supplied from the setting unit 231 to the display apparatus 11. Further, the transmission unit 237 transmits the high resolution image to the recorder 16 or the printer 17 when necessary.

(Description on Phases of Image Pickup Surfaces of Endoscope)

Figure 8:
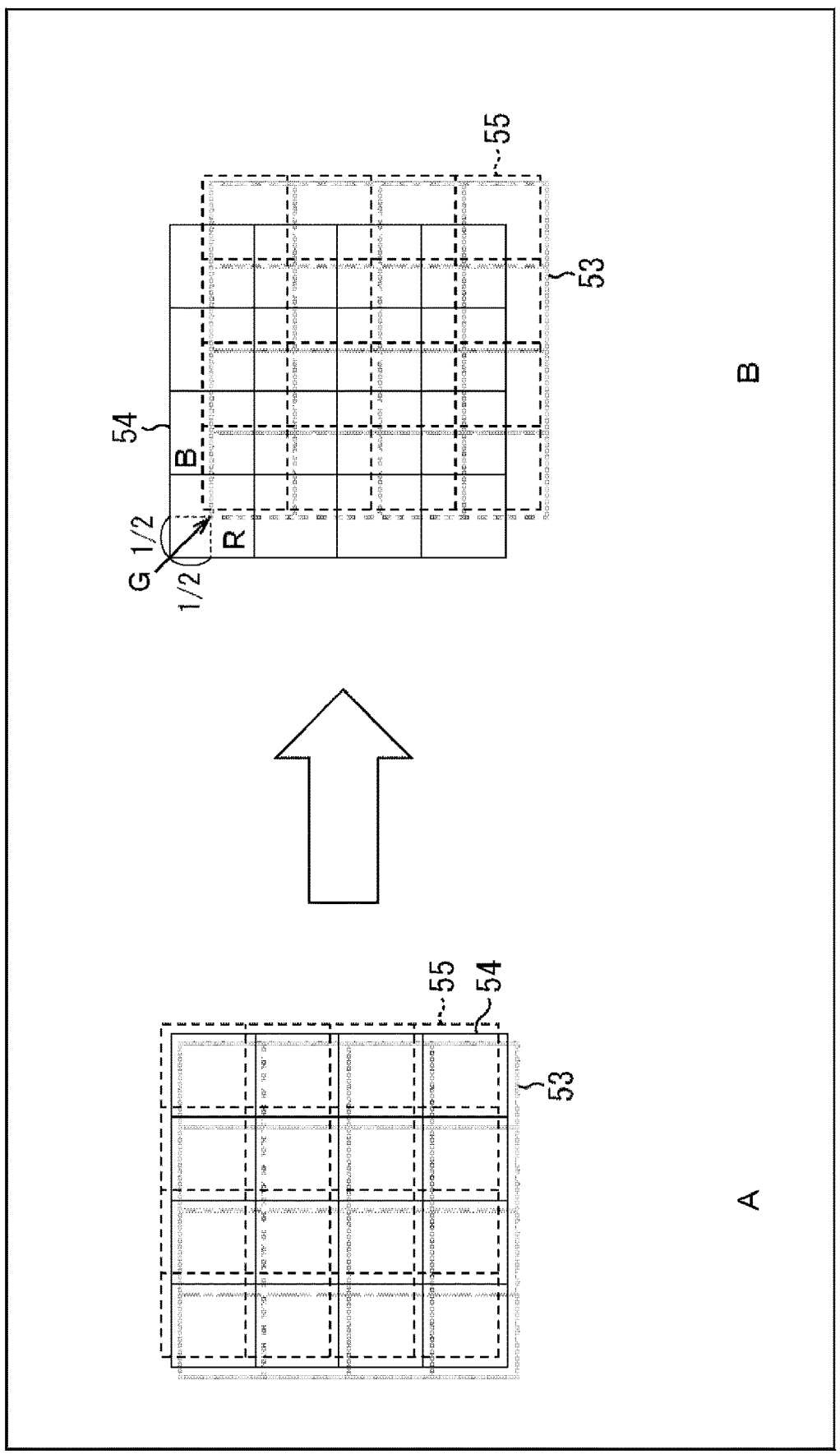
FIG. 8 is a diagram for explaining phases of a red image-pickup surface, a green image-pickup surface, and a blue image-pickup surface.

FIG. 8 is a diagram for explaining the phases of the red image pickup surface 53, the green image pickup surface 54, and the blue image pickup surface 55 of the endoscope 19.

As shown in FIG. 8A, the image pickup unit of the endoscope 19 has the red image pickup surface 53, the green image pickup surface 54, and the blue image pickup surface 55.

Further, as shown in FIG. 8B, the phase of the green image pickup surface 54 and the phase of the red image pickup surface 53 are deviated from each other by ½ pixel in horizontal and vertical directions. The phase of the red image pickup surface 53 and the phase of the blue image pickup surface 55 coincide with each other. Thus, from the HD red, green, and blue images, it is possible to generate a 4 k high resolution image, the resolution in each of the horizontal and vertical directions of which is double of HD.

(Description on Return Process of Red Components of High Resolution Image)

Figure 9:
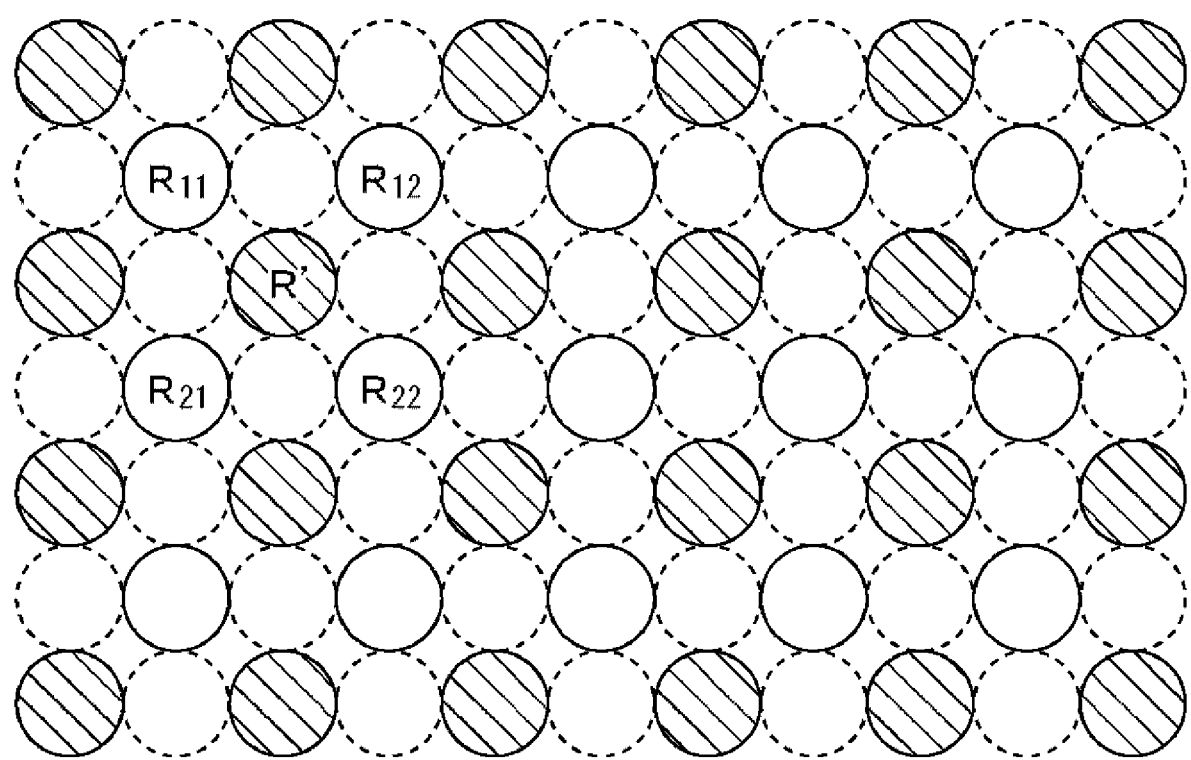
FIG. 9 is a diagram for explaining a return process of red components of a high resolution image.

FIG. 9 is a diagram for explaining the return process of the red components of the high resolution image.

In FIG. 9, solid-line circles without being hatched indicate pixels located on the same position as pixels of the red images (blue images) in the high resolution image, and hatched solid-line circles indicate pixels located on the same position as pixels of the green images. Further, dotted-line circles indicate pixels (hereinafter, referred to as new pixels), the positions of which are different from the pixels of the red image, the green image, and the blue image in the high resolution image.

A red component R' of the pixel located on the same position as the pixel of the green image in the high resolution image can be obtained from the following expression (1) by using the pixels of the red image around the pixel on the basis of a positional relationship between the pixels and the pixel of the red component R', for example.

$$R'=((R_{11}*\alpha+R_{22}*(1-\alpha))+(R_{12}*\beta+R_{21}*(1-\beta)))/2 \quad (1)$$

$R_{11}$, $R_{12}$, $R_{21}$, and $R_{22}$ in the expression (1) are upper left, upper right, lower right, and lower left red image pixels of the pixel corresponding to the red component R', respectively. $\alpha$ and $\beta$ are parameters that vary between 0 and 1 (both inclusive) depending on the deviation amounts from the ideal values of the phases of the red image, the green image, and the blue image. In the case where the deviation amounts from the ideal values of the phases of the red image, the green image, and the blue image are 0, that is, the phases of the red image, the green image, and the blue image are ideal values, both of $\alpha$ and $\beta$ are 0.5.

Thus, a process of obtaining the red component R' from the expression (1) where $\alpha$ and $\beta$ are different is regarded as a candidate of the return process of the red component R' of the high resolution image. Examples of ($\alpha$, $\beta$), which is a combination of values of $\alpha$ and $\beta$ corresponding to the candidate of the return process of the red component R' of the high resolution image include (0.5, 0.5), (0.4, 0.5), (0.5, 0.4), (0.6, 0.5), or the like.

It should be noted that the red components of the new pixels indicated by the dotted-line circles can also be obtained from the expression having parameters that vary depending on the deviation amounts from the ideal values of the phases of the red image, the green image, and the blue image, although detailed description thereof is omitted. Thus, a process of obtaining the red component from the expression having different parameters is regarded as a candidate of the return process for the red components of the new pixels of the high resolution image. Because the phase of the blue image is the same as the phase of the red image, a candidate of the return process for blue components of all pixels of the high resolution image is the same as the candidate of the return process for the red components.

Further, green components of all the pixels of the high resolution image can also be obtained from the expression having parameters that vary depending on the deviation amounts from the ideal values of the phases of the red image, the green image, and the blue image. Thus, a process of obtaining the green components from the expression having different parameters is regarded as a candidate of the return process for the green components of all the pixels of the high resolution image.

The return process candidates of the red components, the green components, and the blue components of the high resolution image are compiled for each of the deviation amounts from the ideal values of the phases of the red image, the green image, and the blue image and regarded as the candidates of the return process.

(Description on Selection of Optimal Return Process)

Figure 10:
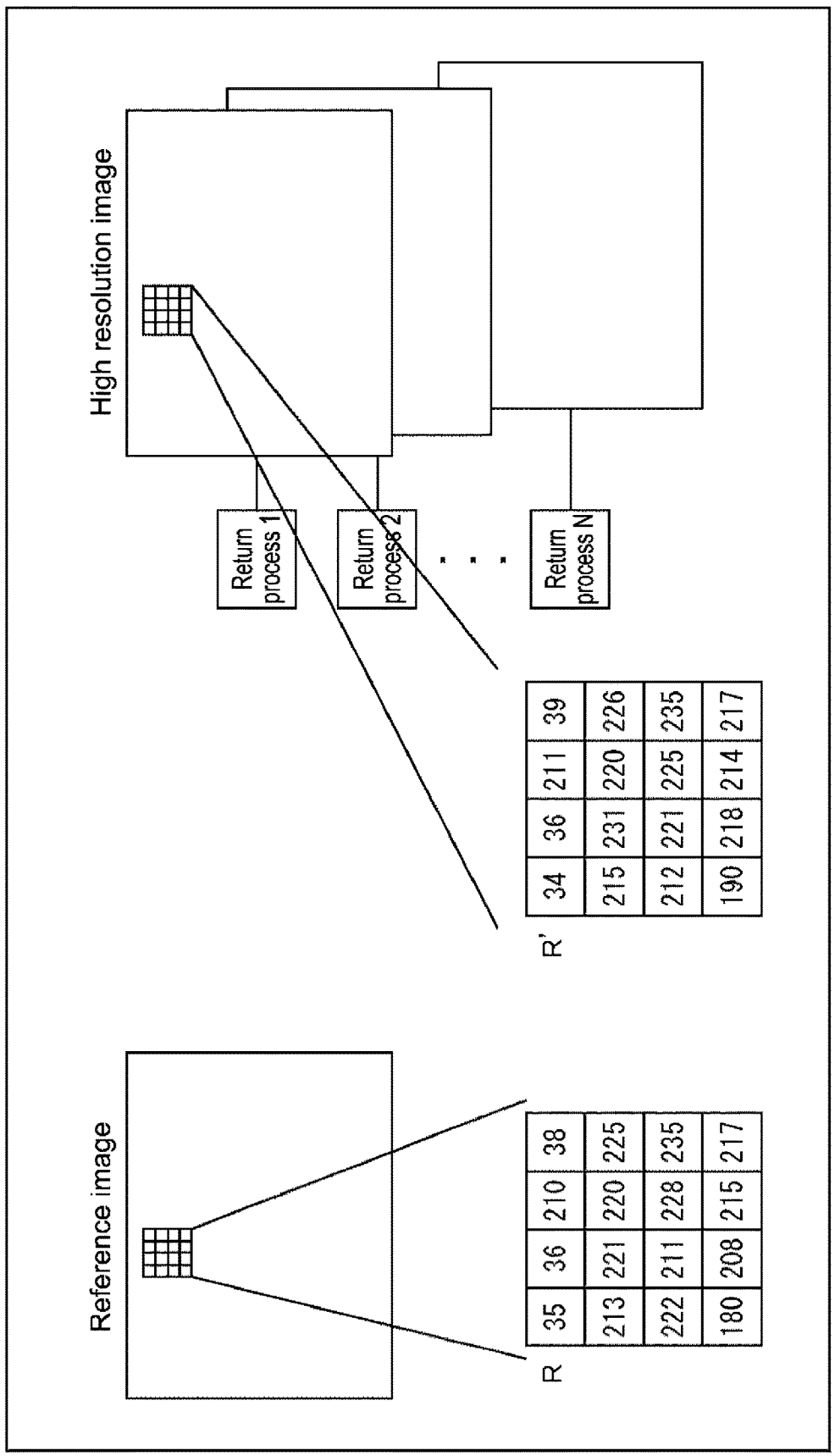
FIG. 10 is a diagram for explaining an optimal return process selection.

FIG. 10 is a diagram for explaining selection of an optimal return process by the selection unit 234 shown in FIG. 7.

As shown in FIG. 10, to the selection unit 234, the reference image and the high resolution image are supplied. From the following expression (2), the selection unit 234 obtains a difference of the red components between the reference image and the high resolution image for each return process candidate.

$$\mathrm{Err}_n=\Sigma(|R(i,j)-R_n'(i,j)|) \quad (2)$$

In the expression (2), $\mathrm{Err}_n$ represents the difference of the red components between the high resolution image generated by the n-th (n=1, 2, ..., N) return process candidate and the reference image. Further, R(i, j) represents the red component of a pixel at a position (i, j) of the reference image, and $R_n'(i, j)$ represents the red component of the pixel at the position (i, j) of the high resolution image generated by the n-th return process candidate.

In accordance with the expression (2), the difference $\mathrm{Err}_n$ is an absolute sum of the difference of the red components of the pixels between the high resolution image and the reference image.

The selection unit 234 also obtains differences of the green components and the blue components in the same way as the difference of the red components between the reference image and the high resolution image. The selection unit 234 adds the differences of the red components, the green components, and the blue components for each return process candidate, and sets the added value as a difference between the reference image and the high resolution image.

The selection unit 234 selects such a return process candidate that the difference between the reference image and the high resolution image is minimum as the optimal return process.

(Description on Process by CCU)

Figure 11:
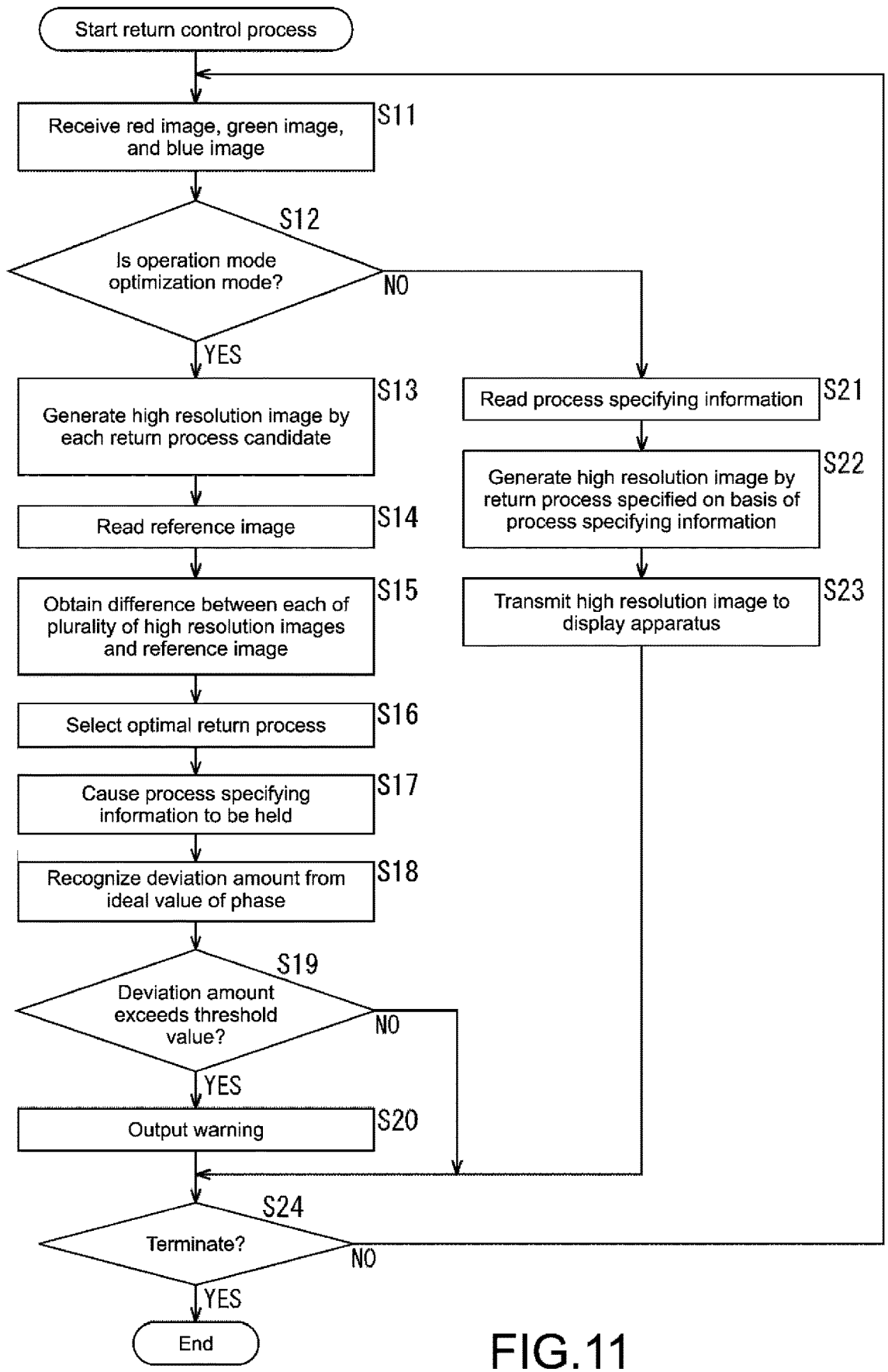
FIG. 11 is a flowchart for explaining a return control process.

FIG. 11 is a flowchart for explaining the return control process by the return control processing unit 230 shown in FIG. 7. The return control process is started when an image is transmitted from the endoscope 19 to the CCU 12, for example.

In Step S11 shown in FIG. 11, the reception unit 232 of the return control processing unit 230 receives the red image, the green image, and the blue image transmitted from the endoscope 19 and supplies the images to the reception unit 232.

In Step S12, the generation unit 233 determines whether the operation mode supplied from the setting unit 231 is the optimization mode or not.

When it is determined that the operation mode is the optimization mode in Step S12, in Step S13, the generation unit 233 uses the red image, the green image, and the blue image supplied from the reception unit 232, to generate high resolution images by each of the return process candidates. The generation unit 233 associates the plurality of generated high resolution images and the process specifying information of the return process candidates at the time of generation of the high resolution images with each other and supplies the associated images and information to the selection unit 234.

In Step S14, the selection unit 234 reads the reference image from the holding unit 235. In Step S15, the selection unit 234 obtains differences between the plurality of high resolution images supplied from the generation unit 233 and the reference image. In Step S16, the selection unit 234 selects, from the return process candidates, one corresponding to the high resolution image with the smallest difference from the reference image as the optimal return process.

In Step S17, the selection unit 234 supplies the process specifying information of the optimal return process to the holding unit 235 and causes the holding unit to hold (update) the information. As a result, until the next process of Step S17, in the process of Step S22 to be described later, the return process specified by the process specifying information is performed.

In Step S18, the selection unit 234 recognizes the deviation amounts from the ideal values of the phases of the red image, the green image, and the blue image corresponding to the optimal return process. In Step S19, the selection unit 234 determines whether the recognized deviation amounts exceed a threshold value or not. When it is determined that the deviation amounts exceed the threshold value in Step S19, the selection unit 234 determines that it is necessary to exchange the endoscope 19 and instructs the warning unit 236 to give a warning.

Then, in Step S20, the warning unit 236 outputs a warning to urge the endoscope 19 to be exchanged, and the process is proceeded to Step S24.

On the other hand, when it is determined that the operation mode is not the optimization mode in Step S12, that is, when the operation mode is the normal mode, the process is proceeded to Step S21. In Step S21, the generation unit 233 reads the process specifying information from the holding unit 235.

In Step S22, by the return process specified by the read process specifying information, the generation unit 233 uses the red image, the green image, and the blue image supplied from the reception unit 232, thereby generating the high resolution image. The generation unit 233 supplies the generated high resolution image to the transmission unit 237.

In Step S23, the transmission unit 237 transmits the high resolution image supplied from the setting unit 231 to the display apparatus 11 and the like, and the process is proceeded to Step S24.

In Step S24, the return control processing unit 230 determines whether the return control process is terminated or not. For example, the return control processing unit 230 determines that the return control process is terminated in the case where image taking by the endoscope 19 is ended, or the power of the CCU 12 is shut off.

When it is determined that the return control process is not terminated in Step S24, the process is returned to Step S11, and until the return control process is determined to be terminated, the process is repeatedly performed.

On the other hand, when it is determined that the return control process is terminated in Step S24, the process is terminated.

As described above, the CCU 12 uses the red image, the green image, and the blue image, thereby generating the high resolution images by the plurality of kinds of return process candidates, and on the basis of the high resolution images, optimal one is selected from the plurality of kinds of return processes. Thus, the CCU 12 generates the high resolution image by the selected optimal return process, with the result that it is possible to sufficiently improve the quality of the high resolution image, even if the phases of the red image pickup surface 53, the green image pickup surface 54, and the blue image pickup surface 55 are deviated from the ideal values.

Further, the return process candidate is a process of generating the high resolution image from the expression using the parameters corresponding to the deviation amounts from the ideal values of the phases of the red image pickup surface 53, the green image pickup surface 54, and the blue image pickup surface 55. Thus, the CCU 12 can recognize the deviation amounts from the optimal return process. As a result, in the case where the deviation amounts exceed the threshold value, it is possible to give a warning for urging the operator or the like to exchange the endoscope 19.

Further, at the time of optimization of the return process, the positional relationship between the chart 42 and the endoscope 19 is fixed by the jig 41, and therefore it is possible to increase the accuracy of the optimization.

Second Embodiment (Description on Phases of Image Pickup Surfaces of Endoscope in Second Embodiment)

A configuration of a second embodiment of an endoscopic surgery system and an optimization system to which the present disclosure is applied is mainly different from the configuration shown in FIGS. 1 and 2 in that the red image pickup surface 53 and the blue image pickup surface 55 of the endoscope 19 have different phases. Thus, hereinafter, description will be given only on the phases of the red image pickup surface 53, the green image pickup surface 54, and the blue image pickup surface 55 of the endoscope 19.

Figure 12:
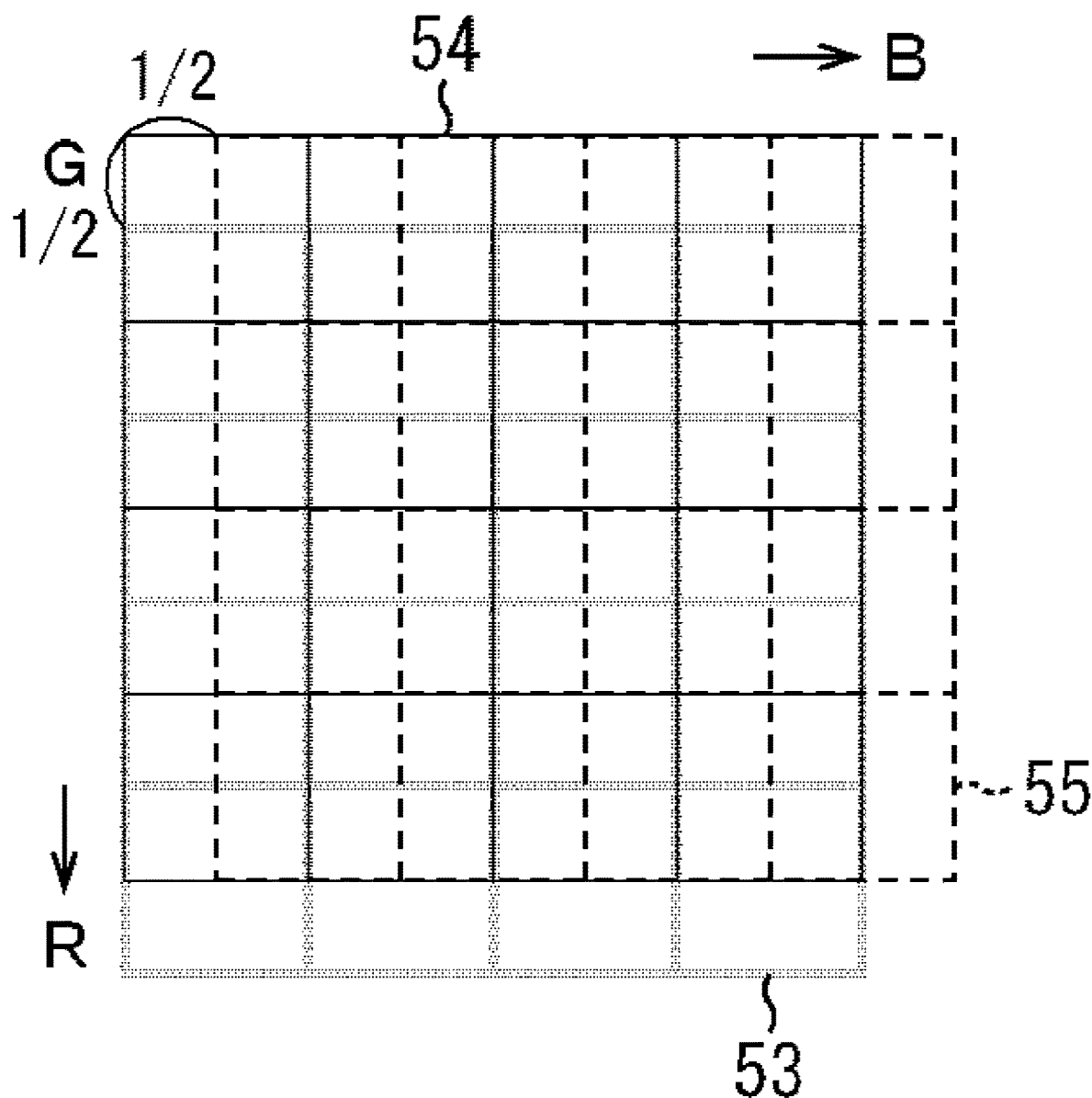
FIG. 12 is a diagram for explaining phases of a red image-pickup surface, a green image-pickup surface, and a blue image-pickup surface in a second embodiment.
Figure 13:
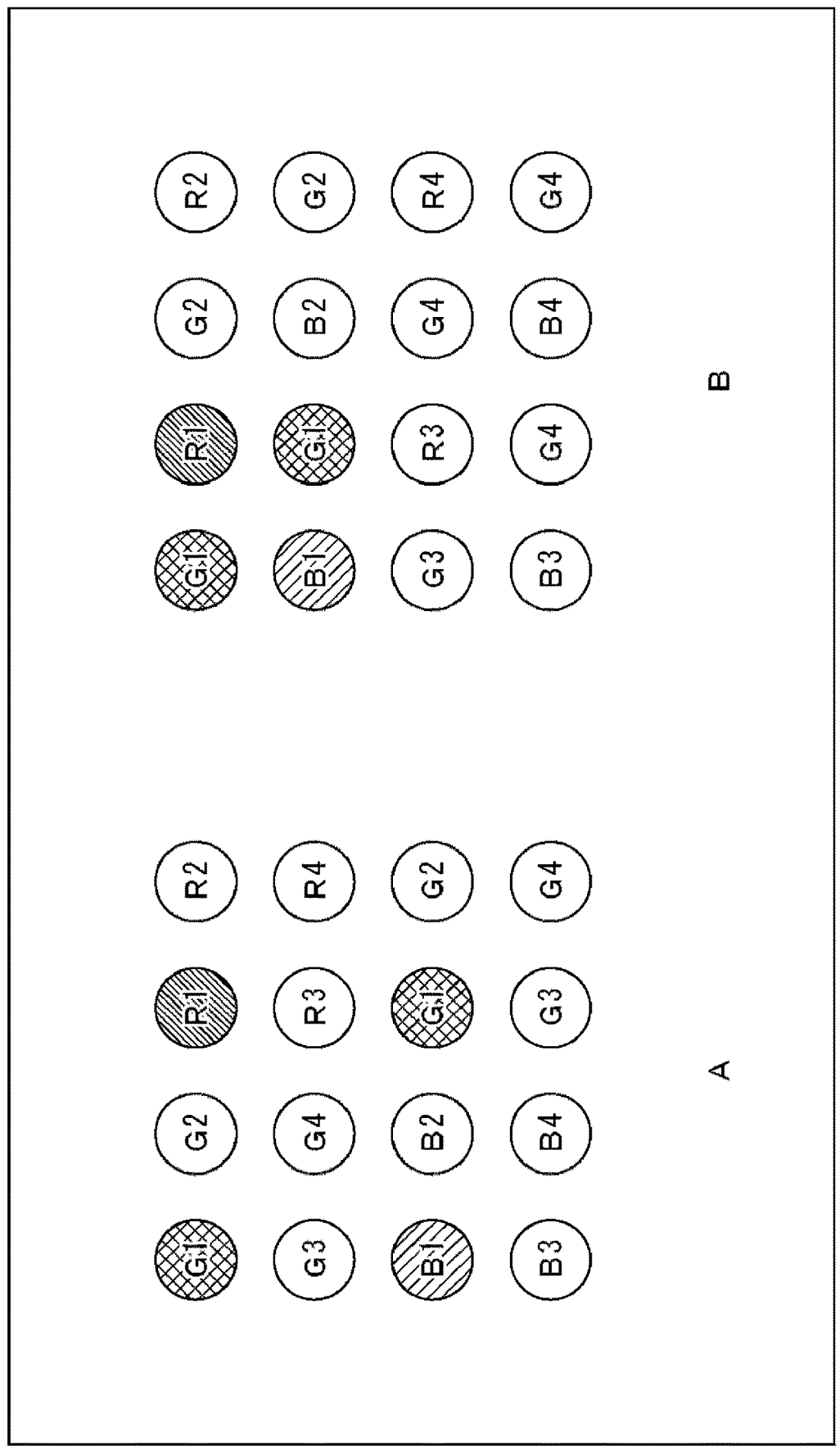
FIG. 13 is a diagram for explaining a pixel shift in a third embodiment.

FIG. 12 is a diagram for explaining the red image pickup surface 53, the green image pickup surface 54, and the blue image pickup surface 55 of the endoscope 19 in the second embodiment.

In the configuration shown in FIG. 12, the same parts as in FIG. 8 are denoted by the same reference numerals. Overlapped description will be omitted as appropriate.

As shown in FIG. 12, in the second embodiment, the phase of the green image pickup surface 54 and the phase of the red image pickup surface 53 are deviated from each other by ½ pixel in the vertical direction. Further, the phase of the green image pickup surface 54 and the phase of the blue image pickup surface 55 are deviated from each other by ½ pixel in the horizontal direction. As a result, from the HD red image, green image, and blue image, it is possible to generate a 4 k high resolution image, the resolution in each of the horizontal direction and the vertical direction of which is double of the HD.

Return process candidates in the second embodiment are different from those in the first embodiment, but are processes of generating a high resolution image from an expression having parameters that vary depending on deviation amounts from ideal values of the phases of the red image, the green image, and the blue image, as in a similar way to the first embodiment.

Third Embodiment (Description on Pixel Shift in Third Embodiment)

A configuration of a third embodiment of an endoscopic surgery system and an optimization system to which the present disclosure is applied is mainly different from the configuration shown in FIGS. 1 and 2 in that the number of image pickup surfaces of the endoscope 19 is one, and pixel shift is carried out by taking images a plurality of number of times while changing the position of the image pickup surface. Thus, hereinafter, only the pixel shift will be described.

FIG. 13 is a diagram for explaining the pixel shift in the third embodiment.

In FIG. 13, description will be given on the pixel shift in 2×2 pixels out of the pixels held by the image pickup surface of the endoscope 19. In FIG. 13, circles indicate the positions of the 2×2 pixels of the image pickup surface of the endoscope 19, and "R", "G", and "B" in the circles represent that the pixels have sensitivities with respect to light of red, green, and blue, respectively. Further, numerals in the circles represent what number of image takings is performed at the position. In the example shown in FIG. 13, the image taking is performed four times, and a color arrangement of the image pickup surface is Bayer arrangement.

In the example shown in FIG. 13A, at the positions indicated by patterned circles, the first image taking is performed with the 2×2 pixels. Subsequently, the image pickup surface of the endoscope 19 is shifted by one pixel rightward (in the row direction) in the figure, and at the positions indicated by circles denoted by 2, the second image taking is performed with the 2×2 pixels.

Then, the image pickup surface of the endoscope 19 is shifted by one pixel in the lower left oblique direction in the figure, and at the position indicated by circles denoted by 3, the third image taking is performed with the 2×2 pixels. Finally, the image pickup surface of the endoscope 19 is shifted by one pixel rightward in the figure, and at the positions indicated by circles denoted by 4, the fourth image taking is performed with the 2×2 pixels. As described above, the pixel shift is performed in which the four HD images having different phases are taken.

On the other hand, in the example shown in FIG. 13B, at the positions indicated by patterned circles, the first image taking is performed with the 2×2 pixels. Subsequently, the image pickup surface of the endoscope 19 is shifted by two pixels rightward in the figure, and at the positions indicated by circles denoted by 2, the second image taking is performed with the 2×2 pixels.

Then, the image pickup surface of the endoscope 19 is shifted by two pixels in the lower left oblique direction in the figure, and at the positions indicated by circles denoted by 3, the third image taking is performed with the 2×2 pixels. Finally, the image pickup surface of the endoscope 19 is shifted by two pixels rightward in the figure, at the positions indicated by circles denoted by 4, the fourth image taking is performed with the 2×2 pixels. As described above, the pixel shift is performed in which the four HD images having different phases are taken.

The return process candidate in the third embodiment is different from that in the first embodiment, but as in the first embodiment, is a process of generating the high resolution image from an expression having parameters that vary depending on the deviation amounts from the ideal values of the phases of the red image, the green image, and the blue image.

It should be noted that, the pixel shift in the third embodiment are not limited to the examples shown in FIG. 13, and the number of image taking times is not limited to four, for example.

The series of processes described above can be executed by hardware.

Further, in this specification, the system means an aggregate of a plurality of components (apparatus, module (part), and the like), and whether all components are in the same casing or not makes no difference. Thus, both of a plurality of apparatuses stored in different casings and connected via a network and one apparatus with a plurality of modules stored in one casing are the systems.

Effects described in this specification are merely examples and are not limited, and other effects may be exerted.

Further, the embodiments of the present disclosure are not limited to the embodiments described above, and can be variously modified without departing from the gist of the present disclosure.

For example, the resolution of the image taken by the endoscope 19 is not limited to HD, and the resolution of the high resolution image is not limited to 4 k. For example, the resolution of the high resolution image can be set to be higher than 4 k resolution such as 8k resolution.

Further, the optimal return process may be selected on the basis of a difference of one component between the high resolution image and the reference image, instead of the sum of all the differences of the red components, the green components, and the blue components therebetween. Further, the optimal return process may be selected for each color.

Furthermore, the number of image pickup surfaces of the endoscope 19 is not limited to three in the first and second embodiments. For example, the endoscope 19 may have a four-plate type image pickup unit constituted of one red image pickup surface, two green image pickup surfaces, and one blue image pickup surface.

The present disclosure can also be applied, in addition to the endoscope, to an image processing apparatus that performs a return process by using images obtained by an image pickup apparatus such as a video microscope that performs pixel shift.

It should be noted that the present disclosure may take the following configurations.

(1)

A medical system, including:

a medical imaging device; and circuitry configured to:

obtain a plurality of first images each having a different phase from the medical imaging device, combine each of the plurality of first images a plurality of times to generate a plurality of second images, wherein each time of the plurality of times that the plurality of first images are combined, a different candidate process is used in the combining, and select one image from the plurality of second images as an output image for display, wherein the selected one image is higher quality than any one of the plurality of first images.

(2)

The medical system according to (1), wherein each of the plurality of first images corresponds to a different color.

(3)

The medical system according to (1) to (2), wherein the circuitry is configured to select the one image from the plurality of second images as the output image based on a reference image.

(4)

The medical system according to (1) to (3), wherein the circuitry is configured to select the one image from the plurality of second images as the output image based on which of the plurality of second images is most similar to the reference image.

(5)

The medical system according to (1) to (4), wherein the circuitry is further configured to compare the selected one image against the reference image to obtain a deviation amount from the reference image.

(6)

The medical system according to (1) to (5), wherein the circuitry is further configured to, when the deviation amount exceeds a predetermined threshold, output a warning.

(7)

The medical system according to (1) to (6), wherein the medical imaging device includes three image sensors.

(8)

The medical system according to (1) to (7), wherein the plurality of second images are each images of a chart having a pattern thereon.

(9)

The medical system according to (1) to (8), wherein the chart is coupled to the medical imaging device via a jig.

(10)

The medical system according to (1) to (9), wherein the selected one image has higher resolution than any resolution of the plurality of first images.

(11)

The medical system according to (1) to (10), wherein the selected one image has more than 4K resolution.

(12)

A medical image processing apparatus, including:
circuitry configured to:
obtain a plurality of first images each having a different phase from a medical imaging device,
combine each of the plurality of first images a plurality of times to generate a plurality of second images, wherein each time of the plurality of times that the plurality of first images are combined, a different candidate process is used in the combining, and select one image from the plurality of second images as an output image for display, wherein the selected one image is higher quality than any one of the plurality of first images.

(13)

The medical image processing apparatus according to (12), wherein each of the plurality of first images corresponds to a different color.

(14)

The medical image processing apparatus according to (12) to (13), wherein the circuitry is configured to select the one image from the plurality of second images as the output image based on a reference image.

(15)

The medical image processing apparatus according to (12) to (14), wherein the circuitry is configured to select the one image from the plurality of second images as the output image based on which of the plurality of second images is most similar to the reference image.

(16)

The medical image processing apparatus according to (15), wherein the circuitry is further configured to compare the selected one image against the reference image to obtain a deviation amount from the reference image.

(17)

The medical image processing apparatus according to (16), wherein the circuitry is further configured to, when the deviation amount exceeds a predetermined threshold, output a warning.

(18)

The medical image processing apparatus according to (12) to (17), wherein the medical imaging device includes three image sensors.

(19)

The medical image processing apparatus according to (12) to (18), wherein the plurality of second images are each images of a chart having a pattern thereon.

(20)

The medical image processing apparatus according to (19), wherein the chart is coupled to the medical imaging device via a jig.

(21)

The medical image processing apparatus according to (12) to (20), wherein the selected one image has higher resolution than any resolution of the plurality of first images.

(22)

The medical image processing apparatus according to (12) to (21), wherein each of the plurality of second images is a high quality image having more than 4K resolution.

(23)

A medical system, including:
a medical imaging device; and
circuitry configured to:
obtain data associated with a plurality of first images each having a different phase from the medical imaging device,
process the data associated with each of the plurality of first images a plurality of times to generate a plurality of second images, wherein each time of the plurality of times that the data associated with the plurality of first images are processed, a different candidate process is used in the processing, and
select one image from the plurality of second images as an output image for display, wherein the selected one image is higher quality than any one of the plurality of first images.

(24)

A medical image processing method, including:
obtaining a plurality of first images each having a different phase from a medical imaging device;
combining each of the plurality of first images a plurality of times to generate a plurality of second images, wherein each time of the plurality of times that the plurality of first images are combined, a different candidate process is used in the combining; and
selecting one image from the plurality of second images as an output image for display,
wherein the selected one image is higher quality than any one of the plurality of first images.

(1A)

A surgery control apparatus, including:
a generation unit configured to perform a plurality of kinds of processes for a plurality of images having different phases which is taken by a surgery image pickup apparatus, thereby generating a plurality of high resolution images having a resolution higher than the plurality of images; and
a selection unit configured to select one of the plurality of kinds of processes on the basis of the plurality of high resolution images generated by the generation unit.

(2A)

The surgery control apparatus according to (1A), in which the generation unit generates the high resolution images having the resolution higher than the plurality of images by performing the process selected by the selection unit for the plurality of images.

(3A)

The surgery control apparatus according to (1A) or (2A), in which the selection unit selects the one of the plurality of kinds of processes on the basis of differences between the respective plurality of high resolution images generated by the generation unit and a reference image.

(4A)

The surgery control apparatus according to (1A), in which the surgery image pickup apparatus takes the plurality of images with a chart included as a subject.

(5A)

The surgery control apparatus according to (4A), in which
the selection unit selects the one of the plurality of kinds of processes on the basis of differences between the respective plurality of high resolution images including the chart as the subject and an ideal high resolution image of the chart.

(6A)

The surgery control apparatus according to (4A) or (5A), in which
the surgery image pickup apparatus takes the plurality of images with a positional relationship between the chart and the surgery image pickup apparatus fixed by a jig.

(7A)

The surgery control apparatus according to any one of (4A) to (6A), in which the chart has a pattern including lattice lines.

(8A)

The surgery control apparatus according to any one of (4A) to (6a), in which the chart has a pattern including vertical lines disposed at different intervals.

(9A)

The surgery control apparatus according to any one of (4A) to (6A), in which the chart has a pattern including vertical lines disposed at intervals longer than a horizontal length of a pixel of at least one image pickup surface of the surgery image pickup apparatus and horizontal lines disposed at intervals longer than a vertical length of the pixel.

(10A)

The surgery control apparatus according to any one of (1A) to (9A), further including a warning unit configured to output a warning on the basis of a deviation amount from an ideal value of the phase which corresponds to the process selected by the selection unit.

(11A)

The surgery control apparatus according to (10A), in which
the warning unit controls a display unit in such a manner that a warning for urging the surgery image pickup apparatus to be exchanged is displayed on the display unit on the basis of the deviation amount.

(12A)

The surgery control apparatus according to any one of (1A) to (11A), in which the surgery image pickup apparatus has a plurality of image pickup surfaces with different phases having sensitivities with respect to light of different colors from each other, and performs image taking on the plurality of image pickup surfaces at the same time, thereby taking the plurality of images.

(13A)

The surgery control apparatus according to any one of (1A) to (11A), in which the surgery image pickup apparatus has one image pickup surface, and performs image taking a plurality of number of times while changing a position of the image pickup surface, thereby taking the plurality of images.

(14A)

The surgery control apparatus according to any one of (1A) to (13A), in which the plurality of high resolution images are images having a resolution of at least 4 k resolution.

(15A)

A surgery control method, including:
performing a plurality of kinds of processes for a plurality of images having different phases which is taken by a surgery image pickup apparatus, thereby generating a plurality of high resolution images having a resolution higher than the plurality of images by a surgery control apparatus; and
selecting one of the plurality of kinds of processes on the basis of the plurality of high resolution images generated in the generation step by the surgery control apparatus.

(16A)

A program for causing a computer to function as
a generation unit configured to perform a plurality of kinds of processes for a plurality of images having different phases which is taken by a surgery image pickup apparatus, thereby generating a plurality of high resolution images having a resolution higher than the plurality of images, and
a selection unit configured to select one of the plurality of kinds of processes on the basis of the plurality of high resolution images generated by the generation unit.

(17A)

A surgery system, including:
a surgery image pickup apparatus configured to take a plurality of images having different phases;
a chart, an image of which is taken by the surgery image pickup apparatus, when a process of generating a high resolution image having a resolution higher than the plurality of images is selected by using the plurality of images taken by the surgery image pickup apparatus; and
a jig configured to fix a positional relationship between the surgery image pickup apparatus and the chart.

It should be understood by those skilled in the art that various modifications, combinations, sub-combinations and alterations may occur depending on design requirements and other factors insofar as they are within the scope of the appended claims or the equivalents thereof.

REFERENCE SIGNS LIST

12 CCU
19 Endoscope
40 Optimization system
41 Jig
42 Chart
53 Red image pickup surface
54 Green image pickup surface
55 Blue image pickup surface
61 Line
62, 72 Vertical line
73 Horizontal line
207 Output unit
233 Generation unit
234 Selection unit
236 Warning unit

The invention claimed is:

1. A medical system, comprising:
a medical imaging device; and
circuitry configured to:
determine whether an operator has set a normal mode or an optimization mode;
during the optimization mode, obtain a plurality of first images each having a different phase from the medical imaging device, the plurality of first images being of a predetermined pattern and different phases being a result of a pixel shift by the medical imaging device,
combine each of the plurality of first images a plurality of times to generate a plurality of second images, wherein each time of the plurality of times that the plurality of first images are combined, a different candidate process is used in the combining, each candidate process generating a high resolution image from an expression having parameters that vary depending on deviation amounts from ideal values for phases of the plurality of first images, and select one image from the plurality of second images as an output image for display based on which of the plurality of second images is most similar to a reference image, wherein the reference image is not a surgical image, wherein the selected one image is higher quality than any one of the plurality of first images, select, as an optimal candidate process, the candidate process used to generate the selected one image, and store the optimal candidate process to be used during the normal mode of the medical imaging device in which a surgical image is obtained.

2. The medical system according to claim 1, wherein each of the plurality of first images corresponds to a different color.

3. The medical system according to claim 1, wherein the circuitry is further configured to compare the selected one image against the reference image to obtain a deviation amount from the reference image.

4. The medical system according to claim 3, wherein the circuitry is further configured to, when the deviation amount exceeds a predetermined threshold, output a warning.

5. The medical system according to claim 1, wherein the medical imaging device includes three image sensors.

6. The medical system according to claim 1, wherein the plurality of second images are each images of a chart having a pattern thereon.

7. The medical system according to claim 6, wherein the chart is coupled to the medical imaging device via a jig.

8. The medical system according to claim 1, wherein the selected one image has higher resolution than any resolution of the plurality of first images.

9. The medical system according to claim 1, wherein the selected one image has more than 4K resolution.

10. A medical image processing apparatus, comprising: circuitry configured to:

determine whether an operator has set a normal mode or an optimization mode;

during the optimization mode, obtain a plurality of first images each having a different phase from a medical imaging device, the plurality of first images being of a predetermined pattern and different phases being a result of a pixel shift by the medical imaging device, combine each of the plurality of first images a plurality of times to generate a plurality of second images, wherein each time of the plurality of times that the plurality of first images are combined, a different candidate process is used in the combining, each candidate process generating a high resolution image from an expression having parameters that vary depending on deviation amounts from ideal values for phases of the plurality of first images, select one image from the plurality of second images as an output image for display based on which of the plurality of second images is most similar to a reference image, wherein the reference image is not a surgical image, wherein the selected one image is higher quality than any one of the plurality of first images, select, as an optimal candidate process, the candidate process used to generate the selected one image, and store the optimal candidate process to be used during the normal mode of the medical imaging device in which a surgical image is obtained.

11. The medical image processing apparatus according to claim wherein each of the plurality of first images corresponds to a different color.

12. The medical image processing apparatus according to claim 10, wherein the circuitry is further configured to compare the selected one image against the reference image to obtain a deviation amount from the reference image.

13. The medical image processing apparatus according to claim 10, wherein the circuitry is further configured to, when the deviation amount exceeds a predetermined threshold, output a warning.

14. The medical image processing apparatus according to claim 10, wherein the medical imaging device includes three image sensors.

15. The medical image processing apparatus according to claim 10, wherein the plurality of second images are each images of a chart having a pattern thereon.

16. The medical image processing apparatus according to claim 15, wherein the chart is coupled to the medical imaging device via a jig.

17. The medical image processing apparatus according to claim 10, wherein the selected one image has higher resolution than any resolution of the plurality of first images.

18. The medical image processing apparatus according to claim 10, wherein each of the plurality of second images is a high quality image having more than 4K resolution.

19. A medical system, comprising:
a medical imaging device; and
circuitry configured to:
during an optimization mode, obtain a plurality of first images each having a different phase from a medical imaging device, the plurality of first images being of a predetermined pattern and different phases being a result of a pixel shift by the medical imaging device, process the data associated with each of the plurality of first images a plurality of times to generate a plurality of second images, wherein each time of the plurality of times that the data associated with the plurality of first images are processed, a different candidate process is used in the processing, each candidate process generating a high resolution image from an expression having parameters that vary depending on deviation amounts from ideal values for phases of the plurality of first images, select one image from the plurality of second images as an output image for display based on which of the plurality of second images is most similar to a reference image, wherein the reference image is not a surgical image, wherein the selected one image is higher quality than any one of the plurality of first images, select, as an optimal candidate process, the candidate process used to generate the selected one image, and store the optimal candidate process to be used during a normal mode of the medical imaging device in which a surgical image is obtained.

20. A medical image processing method, comprising:
determining whether an operator has set a normal mode or an optimization mode;
during the optimization mode, obtaining a plurality of first images each having a different phase from a medical imaging device, the plurality of first images being of a predetermined pattern and different phases being a result of a pixel shift by the medical imaging device;
combining each of the plurality of first images a plurality of times to generate a plurality of second images, wherein each time of the plurality of times that the plurality of first images are combined, a different candidate process is used in the combining, each candidate process generating a high resolution image from an expression having parameters that vary depending on deviation amounts from ideal values for phases of the plurality of first images;

selecting one image from the plurality of second images as an output image for display based on which of the plurality of second images is most similar to a reference image, wherein the reference image is not a surgical image, wherein the selected one image is higher quality than any one of the plurality of first images, selectin, as an optimal candidate process, the candidate process used to generate the selected one image, and storing the optimal candidate process to be used during the normal mode of the medical imaging device in which a surgical image is obtained.

* * * * *